(12) United States Patent
Mann

(10) Patent No.: US 8,168,189 B2
(45) Date of Patent: *May 1, 2012

(54) PROTEIN A COMPOSITIONS AND METHODS OF USE

(75) Inventor: Paul Mann, Albuquerque, NM (US)

(73) Assignee: Protalex, Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/882,057

(22) Filed: Sep. 14, 2010

(65) Prior Publication Data

US 2011/0064762 A1   Mar. 17, 2011

Related U.S. Application Data

(63) Continuation of application No. 11/559,713, filed on Nov. 14, 2006, now Pat. No. 7,807,170, which is a continuation of application No. 10/121,481, filed on Apr. 10, 2002, now Pat. No. 7,211,258.

(51) Int. Cl.
*A61K 39/00* (2006.01)
*A61K 39/38* (2006.01)
*A61K 35/26* (2006.01)

(52) U.S. Cl. .................. 424/184.1; 424/185.1; 424/577

(58) Field of Classification Search ........................ None
See application file for complete search history.

(56) References Cited

U.S. PATENT DOCUMENTS

| | | | |
|---|---|---|---|
| 4,315,028 A | 2/1982 | Scheinberg |
| 4,355,029 A | 10/1982 | Ridolfo |
| 4,402,965 A | 9/1983 | Wyburn-Mason |
| 4,479,934 A | 10/1984 | Sedlacek et al. |
| 4,617,266 A | 10/1986 | Fahnestock |
| 4,628,052 A | 12/1986 | Peat |
| 4,681,870 A | 7/1987 | Balint, Jr. et al. |
| 4,699,783 A | 10/1987 | Terman et al. |
| 4,719,107 A | 1/1988 | Carosella et al. |
| 4,816,441 A | 3/1989 | Zeuthen et al. |
| 4,863,869 A | 9/1989 | Balint |
| 4,925,920 A | 5/1990 | Mannick et al. |
| 5,077,284 A | 12/1991 | Loria et al. |
| 5,084,398 A | 1/1992 | Huston et al. |
| 5,084,559 A | 1/1992 | Profy |
| 5,091,091 A | 2/1992 | Terman |
| 5,122,112 A | 6/1992 | Jones |
| 5,189,014 A | 2/1993 | Cowan, Jr. |
| 5,230,887 A | 7/1993 | Hoffmann et al. |
| 5,277,701 A | 1/1994 | Christie et al. |
| 5,324,707 A | 6/1994 | Yokoyama et al. |
| 5,362,490 A | 11/1994 | Kurimoto et al. |
| 5,422,427 A | 6/1995 | Russell et al. |
| 5,470,578 A | 11/1995 | Aoki et al. |
| 5,633,145 A | 5/1997 | Feldmann et al. |
| 5,662,909 A | 9/1997 | Becker et al. |
| 5,741,488 A | 4/1998 | Feldman et al. |
| 5,782,792 A | 7/1998 | Jones et al. |
| 5,877,147 A | 3/1999 | Pinegin |
| 5,958,966 A | 9/1999 | Mann et al. |
| 5,965,400 A | 10/1999 | Briles et al. |
| 5,985,599 A | 11/1999 | McKenzie et al. |
| 5,997,496 A | 12/1999 | Sekiguchi et al. |
| 6,013,763 A | 1/2000 | Braisted et al. |
| 6,039,946 A | 3/2000 | Strahilevitz |
| 6,042,837 A | 3/2000 | Kalland et al. |
| 6,117,421 A | 9/2000 | Morton et al. |
| 6,221,351 B1 | 4/2001 | Terman |
| 6,242,427 B1 | 6/2001 | Schreiber et al. |
| 6,245,340 B1 | 6/2001 | Youssefyeh |
| 6,251,385 B1 | 6/2001 | Terman |
| 6,312,944 B1 | 11/2001 | Russell et al. |
| 6,447,777 B1 | 9/2002 | Terman et al. |
| 6,555,661 B1 | 4/2003 | Torres et al. |
| 7,163,686 B1 | 1/2007 | Silverman |
| 7,211,258 B2 | 5/2007 | Mann |
| 2005/0113299 A1 | 5/2005 | Mann |

FOREIGN PATENT DOCUMENTS

| | | |
|---|---|---|
| JP | 02011523 | 1/1990 |
| WO | 91/19509 | 12/1991 |
| WO | 97/36614 | 10/1997 |
| WO | 00/69457 | 11/2000 |
| WO | 03/086317 | 10/2003 |

OTHER PUBLICATIONS

Benny et al.; Clinical Evaluation of a Staphylococcal Protein A Immunoadsorption System in the Treatment of Myasthenia Gravis Patients; *Transfusion*, 1999; 39: 682-687.

Caldwell, J., et al., A Pilot Study Using a Staph Protein A Column (Prosorba) to Treat Refractory Rheumatoid Arthritis, J.. Rheumatology, 26:8:1657-1662 (1999).

Catalona, W.J., et al., λ Lambda Inteferon Induced by *S. aureus* Protein A Augments Natural Killing and ADCC, Nature, 291:77-79—(1981).

Cochlovius, B., et al., Therapeutic Antibodies, Modern Drug Discovery, Oct. 2003, 33-38.

Das et al., "Induction of Cell Proliferation and Apoptosis: Dependence on the Dose of the Inducer", *Biochemical and Biophysical Research Communications*, 1999; 260(1): 105-110. Das et al., "Protein A-Activated Rat Splenic Lymphocyte Proliferation Involves Tyrosine Kinase-Phospholipase C-Protein Kinase C Pathway", *Immunopharmacology and Immunotoxicology*, 2000; 22(1): 75-90.

Ezepchuk, Yuri et al., Staphylococcal Toxins and Protein A Differentially Induce Cytotoxicity and Release of Tumor Necrosis Factor-α From Human Keratinocytes, The Journal of Investigative Dermatology, 107(4):603-609 (1996).

Feldman, Anti-TNFα Therapy Is Useful in Rheumatoid Arthritis and Crohn's Disease: Analysis of the Mechanism of Action Predicts Utility in Other Diseases, Transplantation Proceedings, 30:4126-4127 (1998).

Felson, D., et al., The Prosorba Column for Treatment of Refractory Rheumatoid Arthritis, Arthritis & Pheumatism, 42:2153-2159 (1999).

Friedman et al., "Microbial Superantigens as Etiopathogenic Agents in Autoimmunity", *Controversies in Clinical Rheumatology*, 1993; 19(1): 207-222.

(Continued)

*Primary Examiner* — Michail Belyavskyi

(74) *Attorney, Agent, or Firm* — Pillsbury Winthrop Shaw Pittman LLP

(57) ABSTRACT

Methods and compositions for modulating an immune response in a subject are provided. Methods include administering to the subject a composition comprising an effective amount of a lymphocyte differentiation factor, e.g., protein A (PA), sufficient to modulate the immune response. Compositions include a lymphocyte differentiation factor, e.g., protein A (PA), in an amount less than 1 µg.

21 Claims, 3 Drawing Sheets

OTHER PUBLICATIONS

Figure 1:
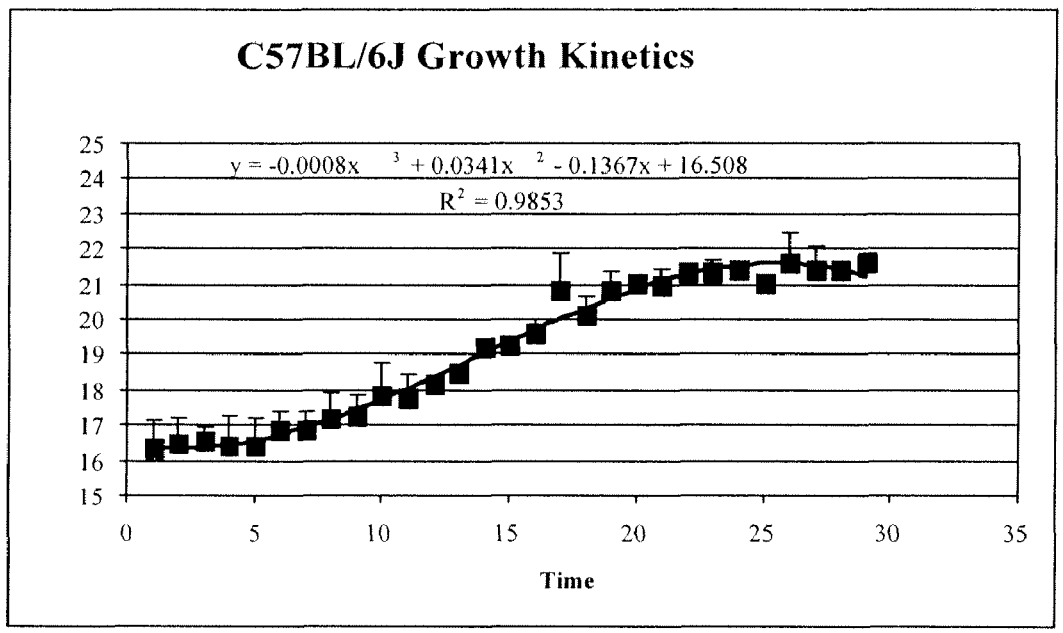
Figure 1:
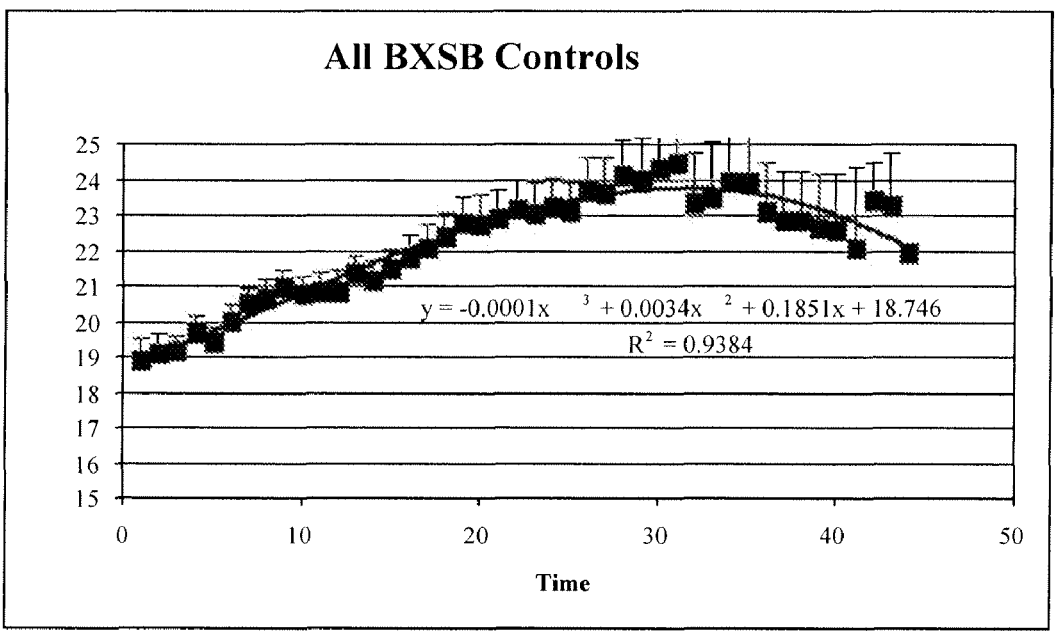
Figure 1C:
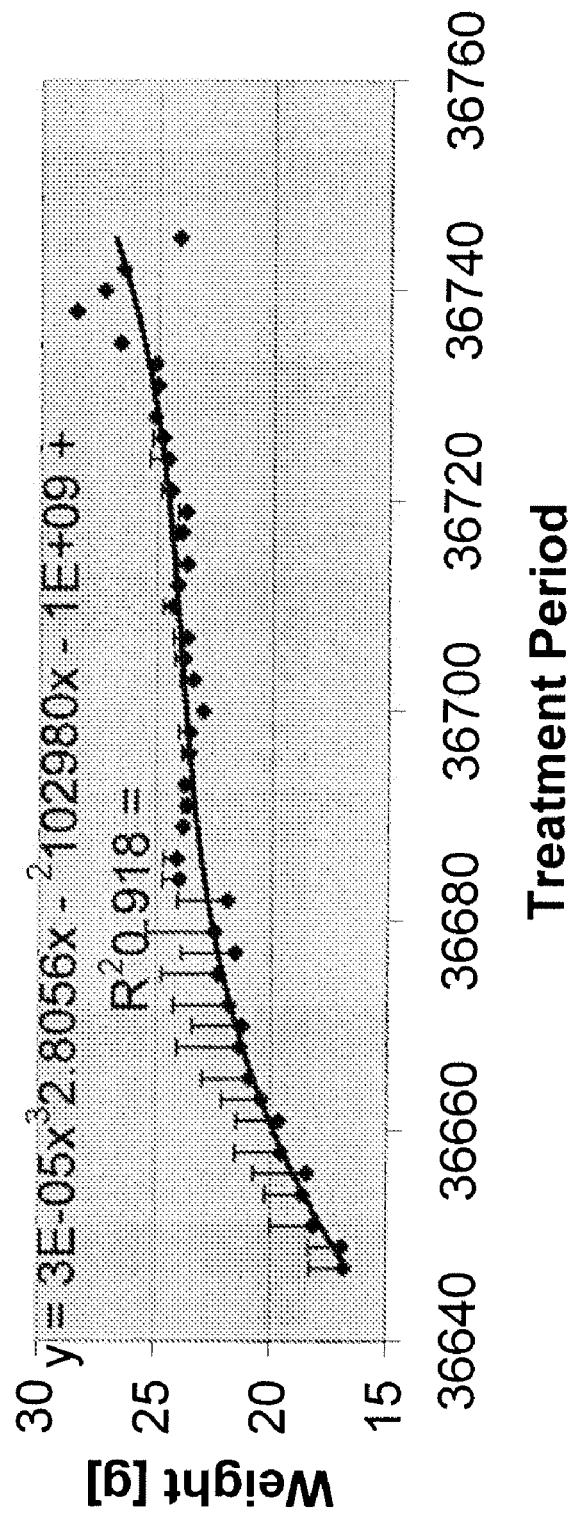

Ghosh et al., "Protection by Protein A of Apoptotic Cell Death Caused by Anti-AIDS Drug Zidovudine", *Biochemical and Biophysical Research Communications*, 1999; 264(2): 601-604.

Ghosh, A.K., et al., *S. aureus* Superantigen Protein A Expands CD4+/CD8+/CD19+/CD34+ Cells in Mice: A Potential Immunorestorer, Biochemical and Biophysical Research Communications, 142-146 (1999).

Goodyear et al., "Evidence Of A Novel Immunomodulatory Mechanism Of Action Of Prosorba Therapy: Release Of Staphyloccoccal Protein A Induces $V_H$ Region Targeted Apoptotic Death Of B Lymphocytes", *Merck's Rheumatology Young Investigators' Program*, 2000;Nov. 14: S296, Abstract #1462.

Graille, Marc et al., Crystal structure of a *Staphylococcus aureus* protein A domain complexed with the Fab fragment of a human IgM antibody: Structural basis for recognition of B-cell receptors and superantigen activity, PNAS, 97(10):5399-5404.

He et al., "Selective Induction of Rheumatoid Factors by Superantigens and Human Helper T Cells", *J. Clin. Invest.*, 1992; 89: 673-680.

Kozlowski et al., "In Vivo Inflammatory Response to a Prototypic B Cell Superantigen: Elicitation of an Arthus Reaction by Staphylococcal Protein A", *Journal of Immunology*, 1998; 160: 5346-5252.

Kozlowski et al., "*Staphylococcus aureus* Cowan I-Induced Human Immunoglobulin Responses: Preferential IgM Rheumatoid Factor Production and VH3 mRNA Expression by Protein A-Binding B Cells", *Journal of Clinical Immunology*, 1995; 15(3): 145-151.

Levinson et al., "Prominent IgM Rheumatoid Factor Production by Human Cord Blood Lymphocytes Stimulated in Vitro With *Staphylococcus aureus* Cowan I", *Journal of Immunology*, 1987; 139(7): 2237-2241.

Levinson et al., "*Staphylococcus aureus* Cowan I: Potent Stimulus of Immunoglobulin M Rheumatoid Factor Production", *Journal of Clinical Investigation*, 1986; 78(3): 612-617.

Levinson, et al., "IgM Rheumatoid Factor Produced in Response to *S. Aureus* Cowan I: Role of Protein A and Preferential Utilization of VH3 Heavy Chains", *The Journal of Immunology*, 1993; 150(8), Part 2, Abstract #1355.

Matic et al., "Background and Indications for Protein A-Based Extracorporeal Immunoadsorption", *Therapeutic Apheresis*, 2001; 5(5): 394-403.

Mestas, J., et al., Of Mice and Not Men: Differences Between Mouse and Human Immunology, The Journal of Immunology, 172:2731-2738 (2004).

Mourad et al., "Engagement of Major Histocompatibility Complex Class II Molecules by Superantigen Induces Inflammatory Cytokine Gene Expression in Human Rheumatoid Fibroblast-like Synoviocytes," *J. Exp. Med.*, 1992; 175: 613-616.

Nardella et al., "IgG Rheumatoid Factors and Staphylococcal Protein A Bind to A Common Molecular Site on IgG," *The Journal of Experimental Medicine*, 1985; 162(6): 1811-1823.

Paliard, X., et al., Evidence for the Effects of a Superantigen in Rheumatoid Arthritis, Science, 325-329 (1991).

Paul, W.E., et al., Fundamental Immunology, 1998, Lippincott-Raven Publisher, pp. 788, 1105.

Rheumawire Dec. 7, 2001 (BR) New mechanism of action proposed for Prosorba column, http://ww.jointandbone.org/news/200112/news20011207a.cfm.

Romagnani, S., et al., Surface Immunoglobulins are Involved in the Interaction of Protein A with Human B Cells and in the Triggering of b Cell Proliferation Induced by Protein A-Containing *Staphylococcus aureus*, The Journal of Immunology, 1307-1313 (1981).

Samtleben, W., et al., Ex vivo and in vivo Protein A Perfusion: Background, Basic Investigations, and First Clinical Experiances, Blood Purification, 5:179-192 (1987).

Schneider, M., et al., Immunoadsorption in Systemic Connective Tissue Diseases and Primary Vasculitis, Therapeutic Apheresis, 1(2):117-120 (1997).

Silverman et al., "A B Cell Superantigen-induced Persisent "Hole" in the B-1 Repertoire", *J. Exp. Med.*, 2000;192(1): 87-98.

Silverman et al., "B-Cell Superantigens: Molecular and Cellular Implications", *Intern. Rev. Immunol.*, 1997; 14: 259-290.

Silverman et al., "In Vivo Consquences of B Cell Superantigen Immunization", *Annals of the New York Academy of Sciences*, 1997; 815: 105-110.

Silverman, Gregg, B cell superantigens: possible roles in Immunodeficiency and autoimmunity, Seminars in Immunology, vol. 10, 43-55 (1998).

Sinha et al., A Minimized Fc Binding Peptide from Protein A Induces Immunocyte Proliferation and Evokes Th1-Type Response in Mice, *Biochemical and Biophysical Research Comunications*, 1999; 258:141-147.

Sinha, P., et al., Protein A of *Staphylococcus aureus* Evokes Th1 Type Response in Mice, Immunology Letters 67:157-165 (1999).

Van Noort, J.M., et al., Cell Biology of Autoimmune Diseases, International Review of Cytology, 178:127-204 (1998).

Wiesenhutter, C.W., et al., Treatment of Patients with Refractory Rheumatoid Arthritis with Extracorporeal Protein A Imunoadsorption Columns: A Pilot Trial, J. Rheumatology, 21:804-812 (1994).

Ghose, A.C., et al., Therapeutic and prophylactic uses of Protein A in the control of *Leishmania donovani* infection in experimental animals, Immunology Letters, 65, 1999, 175-181.

Ray, P.K., et al., Protection of apoptotic cell death by protein A, Apoptosis, 5, 2000, 509-514.

Shukla, Y., et al., Antitumour activity of protein A in a mouse skin model of two-stage carcinogenesis, Cancer Letters, 103, 1996, 41-47.

A.

B.

US 8,168,189 B2

PROTEIN A COMPOSITIONS AND METHODS OF USE

RELATED APPLICATIONS

This application is a continuation application of U.S. application Ser. No. 11/559,713, filed Nov. 14, 2006, now U.S. Pat. No. 7,807,170, which is a continuation application of U.S. application Ser. No. 10/121,481, filed Apr. 10, 2002 now U.S. Pat. No. 7,211,258, all of which applications are expressly incorporated by reference herein in their entirety.

TECHNICAL FIELD

The invention relates to immune response modulation and treating immune disorders and pathologies associated with or caused by immune disorders.

BACKGROUND

Protein A is a 40,000 Da glycoprotein extracted from the cell wall of various bacteria. Bacteria use PA as a targeting and binding site for tissue attachment. Protein A has a high affinity for the Fc portion of certain immunoglobulin classes and even higher affinity for those immunoglobulins once they have bound antigen. This biochemical property of PA has been used in a large number of applications. These applications of PA reflect a use of the Fc binding properties of the molecule or PA's ability to stimulate humoral immunity in the absence of specific antigen induction (Superantigen applications).

SUMMARY

The invention is based at least in part on a feature(s) of PA that is distinct from its Fc binding characteristics and Superantigen properties. This feature confers one or more of the following activities in animals: an ability to re-regulate aberrant process(es) and inhibit tissue damage or reverse at least a portion of existing tissue damage caused by the un-regulated process(es); an ability to re-regulate aberrant or undesirable immune process(es).

The invention therefore provides methods for modulating an immune response in a subject. In one embodiment, a method includes administering to the subject a composition comprising an effective amount of a lymphocyte differentiation factor sufficient to modulate the immune response. In one aspect, the lymphocyte differentiation factor comprises protein A (PA).

Also provided are methods for treating an immune dysfunction in a subject with or at risk of an immune dysfunction. In one embodiment, a method includes administering to the subject a composition comprising an effective amount of protein A (PA) sufficient to treat the immune dysfunction. In one aspect, the immune dysfunction comprises an autoimmune disorder (e.g., rheumatoid arthritis, juvenile rheumatoid arthritis, osteoarthritis, psoriatic arthritis, diabetes mellitus, multiple sclerosis, encephalomyelitis, myasthenia gravis, systemic lupus erythematosis (SLE), autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus, insulin-resistant diabetes mellitus, immune-mediated infertility, autoimmune Addison's disease, pemphigus vulgaris, pemphigus foliaceus, dermatitis herpetiformis, autoimmune alopecia, Vitiligo, autoimmune hemolytic anemia, autoimmune thrombocytopenic purpura, pernicious anemia, Guillain-Barre syndrome, Stiff-man syndrome, acute rheumatic fever, sympathetic ophthalmia, Goodpasture's syndrome, systemic necrotizing vasculitis, antiphospholipid syndrome or an allergy). In another aspect, the immune dysfunction comprises an immunodeficiency (e.g., severe combined immunodeficiency (SCID) such as recombinase activating gene (RAG 1/2) deficiency, adenosine deaminase (ADA) deficiency, interleukin receptor γ chain ($\gamma_C$) deficiency, Janus-associated kinase 3 (JAK3) deficiency and reticular dysgenesis; primary T cell immunodeficiency such as DiGeorge syndrome, Nude syndrome, T cell receptor deficiency, MHC class II deficiency, TAP-2 deficiency (MHC class I deficiency), ZAP70 tyrosine kinase deficiency and purine nucleotide phosphorylase (PNP) deficiency; predominantly antibody deficiencies such as X-linked agammaglobulinemia (Bruton's tyrosine kinase deficiency); autosomal recessive agammaglobulinemia such as Mu heavy chain deficiency; surrogate light chain (γ5/14.1) deficiency; Hyper-IgM syndrome either X-linked (CD40 ligand deficiency) and others; Ig heavy chain gene deletion; IgA deficiency; deficiency of IgG subclasses (with or without IgA deficiency); common variable immunodeficiency (CVID); antibody deficiency with normal immunoglobulins; transient hypogammaglobulinemia of infancy; interferon γ receptor (IFNGR1, IFNGR2) deficiency; interleukin 12 and interleukin 12 receptor deficiency; immunodeficiency with thymoma; Wiskott-Aldrich syndrome (WAS protein deficiency); ataxia telangiectasia (ATM deficiency); X-linked lymphoproliferative syndrome (SH2D1A/SAP deficiency); and hyper IgE syndrome). In yet another aspect, the immune dysfunction comprises an immunodeficiency associated with or secondary to another disease (e.g., chromosomal instability or defective repair such as Bloom syndrome, Xeroderma pigmentosum, Fanconi anemia, ICF syndrome, Nijmegen breakage syndrome and Seckel syndrome; chromosomal defects such as Down syndrome (Trisomy 21), Turner syndrome and Deletions or rings of chromosome 18 (18p− and 18q−); skeletal abnormalities such as short-limbed skeletal dysplasia (short-limbed dwarfism) and cartilage-hair hypoplasia (metaphyseal chondroplasia); Immunodeficiency associated with generalized growth retardation such as Schimke immuno-osseous dysplasia, Dubowitz syndrome, Kyphomelic dysplasia with SCID, Mulibrey's nannism, Growth retardation, facial anomalies and immunodeficiency and Progeria (Hutchinson-Gilford syndrome); immunodeficiency with dermatologic defects such as ectrodactyly-ectodermal dysplasia-clefting syndrome, immunodeficiency with absent thumbs, anosmia and ichthyosis, partial albinism, Dyskeratosis congenita, Netherton syndrome, Anhidrotic ectodermal dysplasia, Papillon-Lefevre syndrome and congenital ichthyosis; hereditary metabolic defects such as acrodermatitis enteropathica, transcobalamin 2 deficiency, type 1 hereditary orotic aciduria, intractable diarrhea, abnormal facies, trichorrhexis and immunodeficiency, methylmalonic acidemia, biotin dependent carboxylase deficiency, mannosidosis, glycogen storage disease, type 1b, Chediak-Higashi syndrome; hypercatabolism of immunoglobulin such as familial hypercatabolism, intestinal lymphangiectasia; chronic muco-cutaneous candidiasis; hereditary or congenital hyposplenia or asplenia; and Ivermark syndrome).

Further provided are methods for reducing an inflammatory response in a subject with or at risk of an inflammatory response. In one embodiment, a method includes administering to the subject a composition comprising an effective amount of protein A (PA) sufficient to reduce an inflammatory response. In one aspect, the inflammatory response is chronic or acute. In another aspect, the inflammatory response is at least in part mediated by an antibody (e.g., one or more auto-antibodies) or at least in part mediated by cellular immunity.

Additionally provided are methods for reducing inflammation in a subject. In one embodiment, a method includes administering to the subject a composition comprising an effective amount of protein A (PA) sufficient to reduce the inflammation. In one aspect, the inflammation is chronic or acute. In another aspect, the inflammation is at least in part antibody or cell mediated. In still another aspect, the treatment results in a reduction in severity of a symptom of inflammation (e.g., swelling, pain, headache, fever, nausea, skeletal joint stiffness, or tissue or cell damage). In yet another aspect, the treatment results in inhibition of antibody production or lymphoid cell proliferation.

Further provided are methods for inhibiting tissue or cell damage in a subject caused by an inflammatory response or inflammation. In one embodiment, a method includes administering to the subject a composition comprising an effective amount of protein A (PA) sufficient to treat inhibiting tissue or cell damage caused by an inflammatory response or inflammation. In one aspect, the tissue or cell damage is caused by a chronic or acute inflammatory response or inflammation. In another aspect, the inflammatory response or inflammation is at least in part antibody or cell mediated. In yet another aspect, the tissue or cell damage is present in thymus, liver, kidney, spleen, skin, or a skeletal joint (e.g., knee, ankle, hip, shoulder, wrist, finger, toe, or elbow). In still another aspect, the treatment results in inhibiting or preventing further tissue or cell damage.

Methods for treating existing tissue or cell damage in a subject caused by an inflammatory response or inflammation are provided. In one embodiment, a method includes administering to the subject a composition comprising an effective amount of protein A (PA) sufficient to treat existing tissue or cell damage caused by an inflammatory response or inflammation. In one aspect, the existing tissue or cell damage is caused by a chronic or acute inflammatory response or inflammation. In another aspect, the inflammatory response or inflammation is at least in part antibody or cell mediated. In yet another aspect, the existing tissue or cell damage is present in thymus, liver, kidney, spleen, skin, or a skeletal joint (e.g., knee, ankle, hip, shoulder, wrist, finger, toe, or elbow). In still other aspects, the treatment results in reversing tissue or cell damage or results in inhibiting or preventing further tissue or cell damage.

Methods of treating splenomegalia in a subject are also provided. In one embodiment, a method includes administering to the subject a composition comprising an effective amount of protein A (PA) sufficient to treat splenomegalia.

Methods of inhibiting proliferation or survival of a splenocyte in a subject having or at risk of having undesirable splenocyte proliferation or survival are additionally provided. In one embodiment, a method includes administering to the subject a composition comprising an effective amount of protein A (PA) sufficient to inhibit proliferation or survival of the splenocyte.

Methods of stimulating differentiation or apoptosis of a splenocyte in a subject having or at risk of having undesirable splenocyte proliferation or apoptosis are further provided. In one embodiment, a method includes administering to the subject a composition comprising an effective amount of protein A (PA) sufficient to stimulate differentiation or apoptosis of the splenocyte.

Methods of reducing antibody production by a splenocyte in a subject having or at risk of having undesirable numbers of an antibody are provided. In one embodiment, a method includes administering to the subject a composition comprising an effective amount of protein A (PA) sufficient to reduce antibody (e.g., auto-antibody) production by a splenocyte.

Methods of reducing numbers of an antibody producing splenocyte in a subject having or at risk of having undesirable numbers of the splenocytes are also provided. In one embodiment, a method includes administering to the subject a composition comprising an effective amount of protein A (PA) sufficient to reduce the antibody (e.g., auto-antibody) producing splenocyte.

Methods of reducing natural killer (NK) cell cytotoxicity in a subject having or at risk of having undesirable NK cell cytotoxicity are additionally provided. In one embodiment, a method includes administering to the subject a composition comprising an effective amount of protein A (PA) sufficient to reduce undesirable NK cell cytotoxicity.

Methods of inhibiting rejection of a transplanted cell, tissue or organ in a subject are further provided. In one embodiment, a method includes administering to the subject a composition comprising an effective amount of protein A (PA) sufficient to inhibit rejection of a transplanted cell, tissue or organ (e.g., an allograft or xenograft). In various aspects, PA is administered prior to, substantially contemporaneously with, or following transplanting the cell, tissue or organ.

Methods of stimulating differentiation of lymphoid cells are provided. In one embodiment, a method includes contacting one or more lymphoid cells in vitro, ex vivo or in vivo with a composition comprising an effective amount of protein A (PA) sufficient to stimulate differentiation of one or more lymphoid cells. In various aspects, the lymphoid cell is a T or B cell.

The invention is also based at least in part on the low amounts of PA required to achieve the activities. In particular, PA has the aforementioned activities at low concentrations, typically less than amounts used for Superantigen applications.

The invention methods therefore may be practiced with PA in amounts effective to elicit one or more of the activities disclosed herein, but without substantial superantigen activity, Fc binding activity or substantially stimulating humoral immunity. In one embodiment, an amount is a dose of about 1 picogram to about 1 microgram of PA. In another embodiment, an amount is a single dose of about 1 picogram to about 1 microgram of PA administered intermittently over about 1 to 15 weeks. In yet another embodiment, an amount is a single dose of about 1 picogram to about 1 microgram administered of PA on alternating days over about 7 to 21 days.

Furthermore, the invention provides compositions that elicit one or more of the activities disclosed herein in unit dosage form. In one embodiment, a composition comprises a unit dosage form of PA from about 0.5-5, 5-10, 10-20, 20-50 or 50-100, 100-500, 100-1000 picograms. In another embodiment, a composition comprises a unit dosage form of PA from about 1-10, 10-100, 100-500 or about 500-1000 nan In yet another embodiment, a composition comprises a unit dosage form of PA sufficient to reduce an inflammatory response or inflammation in a subject.

Pharmaceutical compositions are provided that include a unit dosage form of PA (e.g., 0.5-5, 5-10, 10-20, 20-50 or 50-100, 100-500, 100-1000 picograms; 1-10, 10-100, 100-500 or about 500-1000 nanograms). Pharmaceutical compositions are provided that include a unit dosage form of PA that elicits one or more of the activities disclosed herein (e.g., reduces an inflammatory response or inflammation in a subject).

Kits including a unit dosage form of PA (or pharmaceutical compositions) are also provided, such kits optionally further including instructions for use in a method of the invention (e.g., reducing an inflammatory response, inflammation or tissue or cell damage caused by an inflammatory response or inflammation in a subject). In one embodiment, a kit includes a plurality of unit dosage forms of PA. In another embodiment, a kit further includes a drug (e.g., that reduces an inflammatory response or inflammation).

DESCRIPTION OF DRAWINGS

FIG. 1 shows the weight gain and growth kinetics of A) control untreated normal mice (C57BL/6J); B) untreated BXSB mice; and C) BXSB mice with PA treatment.

FIG. 2 shows data indicating that the E-03 dose of PA rectifies the decrease in CD69−CD4+ observed in BXSB controls at early time points, although later losing this effect at longer time points of chronic treatment.

DETAILED DESCRIPTION

The invention is based at least in part on the characterization of one or more activities of protein A (PA) that appear to be distinct from its Superantigen properties, Fc binding activity or its ability to stimulate humoral immunity. These distinct PA activities are believed to be at least in part attributable to PAs ability to re-regulate or normalize undesirable or aberrant physiological process(es) such as immune dysfunction. PA's ability to re-regulate or normalize physiological process(es) results in many different beneficial activities including, for example, modulating aberrant or undesirable immune response (e.g., re-regulating or normalizing), ameliorating or reducing autoimmunity, reducing inflammation or an inflammatory response, inhibiting or reversing at least a portion of tissue damage caused by an un-regulated process(es) such as an undesirable or aberrant immune response.

More particularly, PA efficacy is demonstrated through the use of a collagen induced arthritis (CIA) murine inflammation model. The induced immune response to Type II collagen is antibody mediated causing a rapidly progressing inflammatory response which can be assessed by measuring the inflammation in affected joints and also by applying a standardized clinical assessment for the affected joints (termed "clinical index" or "CI"). The CI assessment involves both swelling and mobility measures. As shown in Example 1, PA at low concentrations inhibits an acute inflammatory response in the CIA murine model. Histological examination of knee and ankle joints revealed a reduction in tissue damage as well as of immune cell infiltration of the synovium.

PA efficacy is also demonstrated in BXSB animal model, which represents a combined autoimmune deficiency disease having a genetic basis that results in early death of the male animals. As shown in Examples 3 to 8, PA at low concentrations modifies many disease characteristics in the BXSB animal, in many cases re-regulating the various manifestations of the disease (cellular and histological) towards base-line levels (i.e., towards normalization). For example, PA inhibits or prevents the early onset of the wasting (weight loss); regulates expansion of the splenic compartment; inhibits over-expression or -activity of humoral immunity; inhibits over-expression or -activity of cellular immunity; modulates differentiation of cells of lymphoid cell lineage; and ameliorates, reduces or reverses tissue damage caused by or associated with the disease processes. The data further indicates that PA has the same dose response pattern as in the CIA model Thus, PA activities at low concentrations include, for example, one or more of regulating expansion of the splenic compartment (modulating proliferation, apoptosis or differentiation), regulating aberrant or undesirable humoral immunity (inhibiting autoantibody production or inhibiting cells that produce autoantibodies), regulating aberrant or undesirable cellular immunity (normalizing $TH_1/TH_2$ balance, inhibiting cytotoxicity responses), modulating proliferation, apoptosis, or differentiation of cells within the lymphoid cell lineage (e.g., normalizing T cell populations such as increasing numbers of mature T cells, e.g., CD69−CD4+), inhibiting or reversing cell or tissue damage caused by undesirable or aberrant immune response (inhibiting or preventing disease progression, promoting or enhancing disease reversal or tissue regeneration), and normalizing T or B splenocyte numbers or their response to one or more mitogens.

PA is therefore useful in treating a subject in need of one or more of the aforementioned activities associated with PA. The invention therefore provides, inter alia, methods for modulating an immune response (cellular or humoral), methods for treating an undesirable or aberrant immune response (e.g., immune dysfunction) and methods for inhibiting, preventing or reversing a physiological effect caused by or associated with an immune response in a subject. In one embodiment, a method includes administering to a subject a composition comprising an effective amount of a lymphocyte differentiation factor sufficient to modulate the immune response. In another embodiment, a method includes administering to a subject a composition comprising an effective amount of PA sufficient to modulate the immune response.

As used herein, the term "modulate" means a detectable change in an activity or function or effect to which the term is referring. Modulate can mean any increase, decrease, reduction, inhibition, prevention, stimulation, promotion, enhancement in the activity or function or effect to which the term refers. For example, modulating an immune response means that activity or function or an effect of the immune response is detectably changed, e.g., an increase, decrease, reduction, inhibition, prevention, stimulation, promotion, or enhancement of humoral or cell mediated immunity. Changes in an immune response indicative of modulation, including, for example, numbers of T and B cells, proliferation, apoptosis, differentiation, cytotoxicity, antibody production or numbers of antibody producing cells (e.g., autoantibodies), mitogen responsiveness, inflammation, cell or tissue damage, or symptoms thereof, can be measured by a variety of methods disclosed herein or known in the art. An "effective amount" or "sufficient amount" means an amount needed to achieve the activity or effect.

As used herein, the terms "re-regulate," "normalize" and grammatical variations thereof mean a shift towards base line levels. A shift towards base line levels can include, for example, changes in numbers of cells, differentiation status, antibody production or amounts of antibody (e.g., autoantibodies in circulation), cytotoxicity or response to a mitogen. Thus, to re-regulate or normalize numbers of splenocytes in BXSB spleen, for example, means a return towards the number of splenocytes typically found in a normal (e.g., disease free) animal spleen, e.g., C57BL/6. Likewise, to re-regulate or normalize autoantibodies means to reduce the amount of such antibodies to those more typically found in a normal (e.g., disease free) animal. To re-regulate or normalize populations of T cells in BXSB means, for example, to shift the T cell population towards that typically observed in C57BL/6, e.g., a change from immature to a mature T cell population.

The amount of re-regulation or normalization that can occur can be a return to at or near baseline levels typical for a normal animal (within 5-25% of baseline), but may be less, for example, a detectable shift towards baseline levels even though the shift does not return the levels to at or near baseline (e.g., within 25-100% or 25-200% of baseline). The shift will depend on the extent of deviation from baseline in the untreated state, the amount of PA administered and what is being returned to baseline. For example, splenocyte numbers for BXSB are 5 to 6-times greater than C57BL/6. A re-regulation or normalization of splenocyte numbers for BXSB would therefore mean that splenocyte numbers were reduced in BXSB following treatment. For example, a reduction from 5 to 6-times greater than C57BL/6 mice to 1 to 3-times greater than C57BL/6 mice, or more, such as within about 10-50% of splenocyte numbers typically observed in C57BL/6 mice. Similarly, in BXSB there is a 200% increase of ANA at 5 weeks and a 1000% increase of ANA at 11 weeks. A re-regulation or normalization of auto-antibodies for BXSB would therefore mean that auto-antibody numbers (e.g., ANA) were reduced following treatment. For example, treatment with 0.01 µg PA returned these values to at or near baseline (e.g., within 25% of baseline). Thus, autoantibody numbers may decrease from 10-times greater than C57BL/6 mice to 5 to 8-times greater than C57BL/6 mice or to 1 to 5-times greater than C57BL/6 mice, or more, such as within about 10-50% of autoantibody numbers in C57BL/6 mice.

The invention further provides, inter alia, methods for treating an immune dysfunction in a subject with or at risk of an immune dysfunction. In one embodiment, a method includes administering to a subject a composition comprising an effective amount of protein A (PA) sufficient to treat the immune dysfunction. In one aspect, the immune dysfunction comprises an autoimmune disorder.

As used herein, "immune dysfunction" or "immune disorder" means an undesirable immune response, function or activity, that is greater than (e.g., autoimmunity) or less than (e.g., immunodeficiency) desired. An undesirable immune response, function or activity can be a normal response, function or activity. Thus, normal immune responses that are not considered aberrant so long as they are undesirable are included within the meaning of these terms. An undesirable immune response, function or activity can also be an abnormal response, function or activity. An abnormal or an aberrant immune response, function or activity deviates from normal. Immune dysfunction or disorder can be primarily humoral or cellular in nature, or both, either chronic or acute.

Immune dysfunction or disorders include disorders characterized by many different physiological symptoms or abnormalities. As disclosed herein, BXSB mouse model is an immune disorder characterized by a vast array of physiological symptoms and abnormalities which can be treated in accordance with the invention (see for example, Examples 4 to 9). The invention is therefore useful in treating any immune dysfunction or disorder characterized by many different physiological symptoms and abnormalities including disorders having one or more physiological symptoms or abnormalities similar to BXSB mouse model, or equivalent disorders in different species. For example, BXSB mouse is characterized by aberrant splenocyte proliferation, apoptosis or differentiation which leads to expansion of the splenic compartment and a consequent increase in numbers of immature splenocytes. Thus, although the particular types of splenocytes whose numbers increase in BXSB mouse may be different than those of another species with an immune disorder (e.g., with respect to their CD markers), the invention is applicable to any disorder characterized as having undesirable numbers of immature splenocytes (caused by excess cell proliferation, survival or failure of apoptosis) or decreased numbers of mature splenocytes in a subject.

Thus, as the invention is useful for re-regulating or normalizing many facets of an immune response, which leads to ameliorating or reducing one or more of the many different symptoms and abnormalities of the immune disorder, the invention is broadly applicable to disorders that are different from that which occurs in BXSB mouse. Of course, disorders treatable in accordance with the invention include those characterized as having one or more characteristics, symptoms or abnormalities of BXSB even if less severe than those present in BXSB mouse.

Particular examples of immune disorders to which the invention applies include autoimmune disorders and immunodeficiencies. Autoimmune disorders are generally characterized as an undesirable or aberrant response, activity or function of the immune system. Immunodeficiencies are generally characterized by decreased or insufficient humoral or cell-mediated immune responsiveness or memory, or increased or undesirable tolerance. Such disorders that may be treated in accordance with the invention include but are not limited to disorders that cause cell or tissue/organ damage in the subject.

Thus, the invention additionally provides, inter alia, methods for treating an autoimmune disorder in a subject with or at risk of an autoimmune disorder. In one embodiment, a method includes administering to a subject a composition comprising an effective amount of protein A (PA) sufficient to treat the autoimmune disorder. In various aspects, the autoimmune disorder comprises rheumatoid arthritis, juvenile rheumatoid arthritis, osteoarthritis, psoriatic arthritis, diabetes mellitus, multiple sclerosis, encephalomyelitis, myasthenia gravis, systemic lupus erythematosis (SLE), autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus, insulin-resistant diabetes mellitus, immune-mediated infertility, autoimmune Addison's disease, pemphigus vulgaris, pemphigus foliaceus, dermatitis herpetiformis, autoimmune alopecia, Vitiligo, autoimmune hemolytic anemia, autoimmune thrombocytopenic purpura, pernicious anemia, Guillain-Barre syndrome, Stiff-man syndrome, acute rheumatic fever, sympathetic ophthalmia, Goodpasture's syndrome, systemic necrotizing vasculitis, antiphospholipid syndrome or an allergy.

The invention additionally provides, inter alia, methods for treating immunodeficiency in a subject with or at risk of an immunodeficiency. In one embodiment, a method includes administering to a subject a composition comprising an effective amount of protein A (PA) sufficient to treat the immunodeficiency. In various aspects, the immunodeficiency comprises severe combined immunodeficiency (SCID) such as recombinase activating gene (RAG 1/2) deficiency, adenosine deaminase (ADA) deficiency, interleukin receptor γ chain ($γ_C$) deficiency, Janus-associated kinase 3 (JAK3) deficiency and reticular dysgenesis; primary T cell immunodeficiency such as DiGeorge syndrome, Nude syndrome, T cell receptor deficiency, MHC class II deficiency, TAP-2 deficiency (MHC class I deficiency), ZAP70 tyrosine kinase deficiency and purine nucleotide phosphorylase (PNP) deficiency; predominantly antibody deficiencies such as X-linked agammaglobulinemia (Bruton's tyrosine kinase deficiency); autosomal recessive agammaglobulinemia such as Mu heavy chain deficiency; surrogate light chain (γ5/14.1) deficiency; Hyper-IgM syndrome either X-linked (CD40 ligand deficiency) and others; Ig heavy chain gene deletion; IgA deficiency; deficiency of IgG subclasses (with or without IgA deficiency); common variable immunodeficiency (CVID); antibody deficiency with normal immunoglobulins; transient hypogammaglobulinemia of infancy; interferon γ receptor (IFNGR1, IFNGR2) deficiency; interleukin 12 and interleukin 12 receptor deficiency; immunodeficiency with thymoma; Wiskott-Aldrich syndrome (WAS protein deficiency); ataxia telangiectasia (ATM deficiency); X-linked lymphoproliferative syndrome (SH2D1A/SAP deficiency); and hyper IgE syndrome). In yet another aspect, the immune dysfunction comprises an immunodeficiency associated with or secondary to another disease (e.g., chromosomal instability or defective repair such as Bloom syndrome, Xeroderma pigmentosum, Fanconi anemia, ICF syndrome, Nijmegen breakage syndrome and Seckel syndrome; chromosomal defects such as Down syndrome (Trisomy 21), Turner syndrome and Deletions or rings of chromosome 18 (18p– and 18q–); skeletal abnormalities such as short-limbed skeletal dysplasia (short-limbed dwarfism) and cartilage-hair hypoplasia (metaphyseal chondroplasia); Immunodeficiency associated with generalized growth retardation such as Schimke immuno-osseous dysplasia, Dubowitz syndrome, Kyphomelic dysplasia with SCID, Mulibrey's nannism, Growth retardation, facial anomalies and immunodeficiency and Progeria (Hutchinson-Gilford syndrome); immunodeficiency with dermatologic defects such as ectrodactyly-ectodermal dysplasia-clefting syndrome, immunodeficiency with absent thumbs, anosmia and ichthyosis, partial albinism, Dyskeratosis congenita, Netherton syndrome, Anhidrotic ectodermal dysplasia, Papillon-Lefevre syndrome and congenital ichthyosis; hereditary metabolic defects such as acrodermatitis enteropathica, transcobalamin 2 deficiency, type 1 hereditary orotic aciduria, intractable diarrhea, abnormal facies, trichorrhexis and immunodeficiency, methylmalonic acidemia, biotin dependent carboxylase deficiency, mannosidosis, glycogen storage disease, type 1b, Chediak-Higashi syndrome; hypercatabolism of immunoglobulin such as familial hypercatabolism, intestinal lymphangiectasia; chronic muco-cutaneous candidiasis; hereditary or congenital hyposplenia or asplenia; or Ivermark syndrome.

Additional particular examples of immune dysfunction or disorders to which the invention applies include an undesirable or aberrant inflammatory response or inflammation. Such disorders may be mediated by cellular or humoral immunity, or a combination of both.

The invention therefore also provides, inter alia, methods for reducing or inhibiting an inflammatory response or inflammation (chronic or acute) in a subject with or at risk of an inflammatory response or inflammation. In one embodiment, a method includes administering to the subject a composition comprising an effective amount of protein A (PA) sufficient to reduce or inhibit an inflammatory response. In another embodiment, a method includes administering to the subject a composition comprising an effective amount of protein A (PA) sufficient to reduce or inhibit inflammation. In one aspect, the inflammatory response or inflammation is at least in part mediated by an antibody (e.g., one or more autoantibodies). In another aspect, the inflammatory response or inflammation is at least in part mediated by cellular immunity. In various aspects, a method (e.g., treatment) results in a reduction in severity or frequency of a symptom of an inflammatory response or inflammation. In particular aspects, the symptom includes one or more of swelling, pain, headache, fever, nausea, skeletal joint stiffness, or tissue or cell damage. In additional particular aspects, a method (e.g., treatment) results in inhibition of antibody production or lymphoid cell proliferation.

Immune dysfunction, for example, undesirable or aberrant inflammation or an inflammatory response may cause, directly or indirectly, cell or tissue/organ damage, either to multiple cells, tissues or organs, or specifically to a single cell type, organ or tissue type. For example, as disclosed in the Examples, CIA and BXSB models exhibited damage in multiple tissues, as evidenced by changes in histology. Tissues that exhibited damage included knee, ankle, thymus, kidney and liver. Treatment in accordance with the invention resulted in at least a partial reversal of existing tissue damage or a regeneration of normal tissue (see, for example, Tables 9 and 10).

The invention therefore also provides, inter alia, methods for treating, inhibiting and reversing tissue or cell damage, and promoting or enhancing tissue or cell regeneration in a subject caused by immune dysfunction (e.g., an undesirable or aberrant inflammatory response or inflammation). In one embodiment, a method includes administering to a subject a composition comprising an effective amount of protein A (PA) sufficient to treat existing tissue or cell damage caused by immune dysfunction (e.g., an undesirable or aberrant inflammatory response or inflammation). In another embodiment, a method includes administering to a subject a composition comprising an effective amount of protein A (PA) sufficient to inhibit tissue or cell damage (existing or prophylaxis) caused by immune dysfunction (e.g., a chronic or acute undesirable or aberrant inflammatory response or inflammation). In yet another embodiment, a method includes administering to a subject a composition comprising an effective amount of protein A (PA) sufficient to reverse existing tissue or cell damage caused by immune dysfunction (e.g., an undesirable or aberrant inflammatory response or inflammation). In still another embodiment, a method includes administering to a subject a composition comprising an effective amount of protein A (PA) sufficient to promote or enhance tissue or cell regeneration caused by immune dysfunction (e.g., an undesirable or aberrant inflammatory response or inflammation). In one aspect, the inflammatory response or inflammation is at least in part mediated by an antibody (e.g., one or more autoantibodies). In another aspect, the inflammatory response or inflammation is at least in part mediated by cellular immunity. In yet other aspects, the tissue damage is present in thymus, liver, kidney, spleen, skin, or a skeletal joint. In particular aspects, tissue damage in a skeletal joint is present in knee, ankle, hip, shoulder, wrist, finger, toe, or elbow.

Methods of the invention include treatment methods that inhibit or prevent further tissue or cell damage. Thus, the invention also provides methods of treating existing tissue or cell damage in a subject caused by immune dysfunction (e.g., an undesirable or aberrant inflammatory response or inflammation), as well as inhibiting or preventing further tissue or cell damage. In one embodiment, a method includes administering to the subject a composition comprising an effective amount of protein A (PA) sufficient to inhibit or prevent further tissue or cell damage caused by immune dysfunction (e.g., an undesirable or aberrant inflammatory response or inflammation). Examples of existing damage treatable in accordance with the invention include, for example, tissue or organ damage. Exemplary damage as disclosed herein is present in thymus, liver, kidney, spleen, skin, or a skeletal joint (e.g., knee or ankle).

Methods of the invention that include treatment of an inflammatory response or inflammation are desired to reduce a symptom or characteristic of an inflammatory response or inflammation. At the whole body level, an inflammatory response or inflammation is generally characterized by swelling, pain, headache, fever, nausea, skeletal joint stiffness or lack of mobility, redness or other discoloration. At the cellular level, an inflammatory response or inflammation is characterized by one or more of cell infiltration of the region, production of antibodies (e.g., autoantibodies), production of cytokines, lymphokines, chemokines, interferons and interleukins, growth and maturation (e.g., differentiation factors), cell proliferation, differentiation, accumulation or migration and cell, tissue or organ damage. Thus, treatment will reduce, inhibit or prevent one or more of symptoms (severity or frequency of occurrence) or characteristics of an inflammatory response or inflammation.

Methods of the invention also include treating splenomegalia (i.e., enlarged spleen) in a subject. Such methods include administering to the subject a composition comprising an effective amount of protein A (PA) sufficient to treat splenomegalia. Without being bound by any theory, treating splenomegalia typically stimulates, increases or promotes proliferation or survival of mature lymphocytes (e.g., T or B splenocytes), or differentiation from immature to mature cells, or inhibits or decreases proliferation or survival of immature cells to a physiological status more typical of a normal animal, i.e., an animal that does not exhibit splenomegalia. Accordingly, methods for stimulating, increasing or promoting proliferation or survival of mature lymphocytes (e.g., T or B splenocytes) or differentiation from immature to mature lymphocytes (e.g., T or B splenocytes), and inhibiting or decreasing proliferation or survival of immature lymphocytes (e.g., T or B splenocytes), are provided.

Methods of the invention further include inhibiting, reducing or preventing antibody production in a subject. In one embodiment, a method includes administering to a subject having an undesirable antibody or an aberrant antibody a composition comprising an effective amount of protein A (PA) sufficient to reduce antibody production. Autoantibodies are but one example of an antibody in which it may be desired to inhibit, reduce or prevent its production. Antibody production can be inhibited, reduced or prevented either directly, by causing the cell (e.g., splenocyte) that produces the antibody to reduce antibody production, or indirectly, by reducing numbers of cells (e.g., splenocytes) that produce the antibody.

Methods of the invention additionally include inhibiting, reducing or preventing natural killer (NK) cell cytotoxicity in a subject having or at risk of having undesirable NK cell cytotoxicity. In one embodiment, a method includes administering to a subject a composition comprising an effective amount of protein A (PA) sufficient to inhibit, reduce or prevent undesirable NK cell cytotoxicity.

Methods of the invention moreover include stimulating, promoting or enhancing differentiation of a lymphoid cell. In one embodiment, a method includes contacting a lymphoid cell in vitro, ex vivo or in vivo with a composition comprising an effective amount of protein A (PA) sufficient to stimulate, promote or enhance differentiation of a lymphoid cell.

The term "contacting" means direct or indirect binding or interaction between two or more entities (e.g., between PA and a cell or molecule). Contacting as used herein includes in solution, in solid phase, in vitro, in a cell and in vivo.

Assays for detecting an activity of PA include; cellular changes in lymphocyte numbers, proliferation, apoptosis or survival and differentiation include trypan blue exclusion (viability); changes in cellular CD markers or other molecules (differentiation); amounts of antibody (e.g., circulating autoantibodies can be measured using ELISA or other antibody detection assays); tissue or organ improvement including inhibiting further damage or reversing existing tissue damage (histology, tissue or organ function, or enzyme levels indicative of improved function); whole body effects (weight gain or a decrease in weight loss or wasting, improved mobility); and expansion of spleen (histology, numbers of lymphocytes and their differentiation state) as disclosed herein and further known in the art.

As the invention can be used to inhibit, reduce or prevent an undesirable immune response in a subject, further provided are methods for inhibiting, reducing or preventing rejection of a transplanted cell, tissue or organ in a subject (i.e., Host v. Graft disease). In one embodiment, a method includes administering to a subject a composition comprising an effective amount of protein A (PA) sufficient to inhibit, reduce or prevent rejection of a transplanted cell, tissue or organ. Exemplary cells include neural cells. Exemplary tissues include skin, blood vessel, eye and bone marrow. Exemplary organs include heart, lung, liver and kidney. In various aspects, PA is administered prior to, substantially contemporaneously with, or following transplanting the cell, tissue or organ. The transplanted cell, tissue or organ may be an allograft or xenograft.

As used herein, the terms "transplant," "transplantation" and grammatical variations thereof mean grafting, implanting, or transplanting a cell, tissue or organ from one part of the body to another part, or from one individual/animal to another individual/animal. The term also includes genetically modified cells, tissue and organs, e.g., by ex vivo gene therapy in which the transformed cells, tissue and organs are obtained or derived from the person who then receives the transplant, or from a different person/animal.

Methods and compositions of the invention may be used in vitro, ex vivo or in vivo. Compositions can be administered as a single or multiple dosage form, on consecutive or alternating days or intermittently. For example, single or multiple dosage forms can be administered on alternating days or intermittently, over about 7 to 45 days or over about 1 to 15 weeks. In one embodiment, a composition is administered as a single dose on alternating days for between 3 and 5 weeks.

Treatment usually results in an improvement in the subject's condition, that is a change beneficial to the subject, tissue or cell or cell population in the subject that is detectable. Thus, treatment can result in inhibiting, reducing or preventing a progression or worsening of the condition or disorder or symptoms, or further deterioration or onset of one or more additional symptoms of the condition or disorder. Thus, a successful treatment outcome leads to a "therapeutic effect," or inhibiting, reducing or preventing the severity or frequency of symptoms or underlying causes of a disorder or condition in the subject. Stabilizing a disorder or condition is also a successful treatment outcome. Therefore, treatment can reduce or prevent severity or frequency of one or more symptoms of the condition or disorder, inhibit progression or worsening of the condition or disorder, and in some instances, reverse the condition or disorder. Thus, in the case of an immune disorder, for example, treatment can lead to an improvement of a histopathological change caused by or associated with the immune disorder, for example, preventing further or reducing or regenerating skeletal joint infiltration or tissue destruction, or thymus, kidney, liver, spleen, or skin tissue infiltration or tissue destruction.

Treatment also includes affecting the underlying causes of the condition or disorder or symptoms thereof. Thus, in the case of an immune disorder, for example, re-regulating or normalizing absolute numbers of lymphocytes (e.g., splenocytes) or numbers of mature lymphocytes towards normal baseline is considered a successful treatment outcome. Similarly, a reduction of circulating antibodies (e.g., autoantibodies) towards normal baseline is considered a successful treatment outcome.

The term "ameliorate" means a detectable improvement in the subject's overall condition. A detectable improvement includes a subjective reduction in the severity or frequency of symptoms caused by or associated with the disorder or condition, an improvement in the underlying causes of the disorder or condition, or a reversal of the disorder or condition, which is detectable using an assay.

Methods of the invention may be practiced prior to (i.e. prophylaxis) or after symptoms begin, before or after symptoms or the disorder develop (e.g., before cell, tissue or organ transplantation). Administering a composition prior to or immediately following development of symptoms may decrease the severity or frequency of the symptoms in the subject. In addition, administering a composition prior to or immediately following development of symptoms may decrease or prevent damage to cells, tissues and organs that occurs, for example, during immune dysfunction (e.g., autoimmunity).

The term "subject" refers to animals, typically mammalian animals, such as a non-human primate (gorillas, chimpanzees, orangutans, macaques, gibbons), a domestic animal (dogs and cats), a farm animal (horses, cows, goats, sheep, pigs), experimental animal (mouse, rat, rabbit, guinea pig) and humans. Human subjects include adults and children. Human subjects include those having or at risk of having immune dysfunction. At risk subjects can be identified through genetic screening. Particular examples of genetically linked immune disorders that may be identified include X-linked severe combined immunodeficiency, Adenosine deaminase deficiency, DiGeorge Anomaly, Ataxia-telangiectasia, Wiscott-Aldrich Syndrome, Leukocyte adhesion deficiency, and Myotonic dystrophy. These and other disorders are detectable through fetal blood or amniotic cells, or through adult tissue samples as described in Samter's Immunologic Diseases; M M Frank, K F Austen, H N Claman, and E R Unanue editors; Little, Brown and Company. Reviewing family history may be used to detect inheritance patterns or an increased risk (predisposition) of developing the disorder (e.g., autoimmunity or immunodeficiency). At risk subjects may also be identified by screening for a specific characteristic, such as the presence of undesirable or aberrant populations of lymphocytes (e.g., splenocytes) or autoantibodies. At risk subjects include those in need of a cell, tissue or organ transplant. Subjects further include disease model animals (e.g., such as mice and non-human primates) for testing in vivo efficacy of the compositions of the invention (e.g., CIA, BXSB, EAE and SCID murine models).

The invention is practiced with compounds known as "lymphocyte differentiation factors," which are molecules capable of regulating or modulating cell signaling or response to signaling, which in turn can re-regulate, normalize or modulate cell behavior of the cell itself, other cells or processes in which the cells participate (e.g., immune system function). As set forth herein, a specific example of a lymphocyte differentiation factor is PA. Lymphocyte differentiation factors can be used in accordance with the invention in low amounts as set forth herein for PA.

The invention is also based at least in part on the low amounts of PA that can produce one or more of activities disclosed herein. For example, PA at $1\times10^{-5}$ µg ($1\times10^{-11}$ G) per dose administered on alternating days (M/W/F) starting at the time of secondary antigen induction regulated expression and/or progression of the ensuing inflammatory response and regulated expression and/or reversed the tissue damage caused by the inflammatory response. However, at this amount of PA, there was no substantial superantigen activity or stimulation of humoral immunity.

The invention therefore also provides compositions, including PA in an amount that is able to produce one or more of the activities associated with PA, without producing substantial superantigen activity, substantial stimulation of humoral immunity or is substantially independent of Fc binding. Activities of PA in such amounts include, for example, re-regulating or normalizing aberrant or undesirable humoral or cellular immune response (modulating lymphocyte proliferation, apoptosis or differentiation), inhibiting, reversing, ameliorating or reducing autoimmunity, inflammation or an inflammatory response, or at least a portion of tissue damage caused by an undesirable or aberrant immune response (inhibiting or preventing disease progression, promoting or enhancing disease reversal or tissue regeneration), and normalizing T or B splenocyte numbers or their response pattern to one or more mitogens.

Thus, in one embodiment, a composition includes PA in an amount sufficient to modulate lymphocyte proliferation, apoptosis or differentiation. In another embodiment, a composition includes an amount of PA in an amount sufficient to inhibit, reverse, ameliorate or reduce autoimmunity, inflammation or an inflammatory response. In yet another embodiment, a composition includes an amount of PA in an amount sufficient to inhibit, reverse, ameliorate or reduce at least a portion of cell, tissue or organ damage caused by an undesirable or aberrant immune response. In still other embodiments, a composition includes an amount of PA in an amount sufficient to re-regulate or normalize T or B splenocyte numbers or their response to one or more mitogens. In one aspect, the amount of PA is less than 1 μg. In another aspect, the amount of PA is less than 1 μg but greater than 0.01 picograms (pG). In yet another aspect, the amount of PA is less than 0.5 to 0.1 μg but greater than 0.1 pG. In still another aspect, the amount of PA is less than 0.1 to 0.01 μg but greater than 1 pG. In additional aspects, the amount of PA is less than 1 to 0.1 μg but greater than 1 pG; less than 0.1 to 0.01 μg but greater than 1 pG; less than 0.01 to 0.001 μg but greater than 1 pG; less than 1 to 0.5 ng but greater than 1 pG; less than 500 to 250 pG but greater than 1 pG; less than 250 to 50 pG but greater than 5 pG; and less than 50 to 25 pG but greater than 5 pG, e.g., 20, 15, or about 10 pG. In yet additional aspects, the amount of PA does not produce substantial superantigen activity, substantial stimulation of humoral immunity or is substantially independent of Fc binding.

As used herein, the phrases "without substantial" or "substantially independent," when used in reference to superantigen activity, stimulation of humoral immunity or Fc binding of PA, means that the characteristic referred to does not contribute significantly to the observed activity of PA at that amount. Thus, an amount of PA that does not produce substantial superantigen activity means that PA's superantigen activity does not contribute significantly to the activity of that amount of PA. Similarly, an amount of PA that does not produce substantial stimulation of humoral immunity may produce a small amount of humoral activity but again the immunity produced does not contribute significantly to PA's activity at the amount of PA used. Likewise, an amount of PA that is substantially independent of Fc binding means that Fc binding does not contribute significantly to PA's activity at the amount of PA used. In other words, removing or impairing the Fc function of PA would not destroy PA's activity at the amount used. In general, at the low amounts of PA used, superantigen activity, stimulation of humoral immunity or Fc binding of PA does not contribute significantly to PA's activity.

Superantigen activity is typically characterized by the stimulation of non-specific subsets of T cells to proliferate. That is, T cell proliferation is largely independent of epitope specificity. Superantigen activity typically stimulates about 5-10% of T cells to proliferate whereas a conventional antigen may stimulate about 1 in $10^6$ cells in an individual. Superantigen activity may therefore be assayed by determining numbers of T cells that are stimulated to proliferate. Examples of such assays are described, for example, in Johnson et al., Scientific American, April 1992. pp. 92-101; and Kotzin et al., Adv. Immunol. 54:99 (1993). Superantigen and FC binding assays are described, for example, in Romagnani et al., J. Immunol. 129:596 (1982). FC binding assays are described, for example, in Langone J J, Adv. Immunol. 32:157 (1982). Stimulation of humoral immunity assays are described, for example, in Leonetti et al., J. Exp. Med. 189:1217 (1999).

Methods of the invention can therefore be practiced using the compositions of the invention. For example, in one embodiment, an effective amount of PA is a dose of about 0.1 picogram to about 1 microgram. In another embodiment, an effective amount of PA is a dose of about 1 picogram to about 1 microgram. In yet another embodiment, an effective amount of PA is a dose of about 10 picograms to about 1 microgram. In still another embodiment, an effective amount of PA is a dose of about 10 picograms to about 0.1 microgram. In additional embodiments, an effective amount of PA is a single dose of about 10 picograms to about 0.1 microgram.

Compositions may be administered systemically or locally by any route. For example, PA may be administered intravenously, orally (e.g., ingestion or inhalation), intramuscularly, intraperitoneally, intradermally, subcutaneously, intracavity, intracranial, transdermally (topical), parenterally, e.g. transmucosal and rectally. Compositions of the invention including pharmaceutical formulations can be administered via a microencapsulated delivery system or packaged into an implants for administration.

Compositions further include pharmaceutical formulations containing PA in an amount having one or more of the activities disclosed herein. In various embodiments, a pharmaceutical formulation includes PA in an amount sufficient to re-regulate or normalize aberrant or undesirable humoral or cellular immune response (modulating lymphocyte proliferation, apoptosis or differentiation), inhibit, reverse, ameliorate or reduce autoimmunity, inflammation or an inflammatory response, or at least a portion of tissue damage caused by an undesirable or aberrant immune response (inhibiting or preventing disease progression, promoting or enhancing disease reversal or tissue regeneration), normalize T or B splenocyte numbers or their response to one or more mitogens, without substantial superantigen activity, without substantial stimulation of humoral immunity or substantially independent of Fc binding, and a pharmaceutically acceptable carrier or excipient.

As used herein, the terms "pharmaceutically acceptable" and "physiologically acceptable" refer to carriers, excipients, diluents and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. Thus, pharmaceutical formulations include carriers, diluents, or excipients suitable for administration by routes including intraperitoneal, intradermal, subcutaneous, oral (e.g., ingestion or inhalation), intravenous, intracavity, intracranial, transdermal (topical), parenteral, e.g. transmucosal and rectal.

Solutions or suspensions used for parenteral, intradermal, or subcutaneous application can include the following: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical formulations suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride, can be included in the composition. Prolonged absorption of injectable formulations can be achieved by including an agent that delays absorption, for example, aluminum monostearate or gelatin.

For oral administration, a composition can be incorporated with excipients in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including materials that slowly degrade within the body and in turn release the active ingredient(s). For example, a time delay material such as glyceryl monostearate or glyceryl stearate alone, or in combination with a wax, may be employed.

Additional formulations include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. Methods for preparation of such formulations will be apparent to those skilled in the art. The materials can also be obtained commercially from Alza Corporation and Nova Pharmaceuticals, Inc., for example.

The rate of release of a composition can be controlled by altering the concentration or composition of such macromolecules. For example, the composition can be entrapped in microcapsules prepared by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems including oil-in-water emulsions, micelles, mixed micelles, and liposomes. These can be prepared according to methods known to those skilled in the art, for example, as described in U.S. Pat. No. 4,522,811.

Additional pharmaceutical formulations appropriate for administration are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; and *Pharmaceutical Principles of Solid Dosage Forms*, Technonic Publishing Co., Inc., Lancaster, Pa., (1993)).

Compositions of the invention can include combinations of other compositions, and be included in the pharmaceutical compositions of the invention. For example, a drug that reduces an inflammatory response or inflammation or that stimulates differentiation of a cell can be included with a low amount of PA. Exemplary drugs include steroidal (SAI) and non-steroidal anti-inflammatory's (NSAI), for example, a corticosteroid, a cox-2 inhibitor, or drugs that affect the immune system such as chemokines and cytokines such as interleukins and interferons.

Compositions of the invention, including pharmaceutical formulations can be packaged into kits, which optionally can contain instructions for use, for example, practicing a method of the invention. The invention therefore provides kits. In one embodiment, a kit includes one or more compositions of the invention (e.g., PA), including pharmaceutical formulations, packaged into suitable packaging material. In additional embodiments, a kit includes a label or packaging insert for practicing a method of the invention. Thus, in one embodiment, a kit includes instructions for treating a subject having or at risk of having an immune disorder or dysfunction, in vitro, in vivo, or ex vivo. In yet additional embodiments, a kit includes a label or packaging insert including instructions for treating a subject having an autoimmune disorder with low amounts of PA in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention. Kits of the invention therefore can additionally include instructions for using the kit components in a method of the invention.

Instructions can include instructions for practicing any of the methods of the invention described herein. Thus, invention pharmaceutical compositions can be included in a container, pack, or dispenser together with instructions for administration to a subject. Instructions may additionally include indications, a satisfactory clinical endpoint, any adverse symptoms that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice or video tape which can optionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can also include one or more drugs that provide a synergistic or additive effect or that reduce or ameliorate one or more symptoms of a drug or disorder. For example, a drug that reduces an inflammatory response or inflammation may be included. Exemplary drugs include steroidal (SAI) and non-steroidal anti-inflammatory's (NSAI), for example, a corticosteroid, or a cox-2 inhibitor. Invention kits can additionally include a buffering agent, a preservative, or a stabilizing agent. The kit can further include control components for assaying an activity or effect of treatment. Each component of the kit can be enclosed within a separate individual container. For example, a kit can include a single unit dosage of a low amount of PA as set forth herein (e.g., from less than 1 µg to 1 pG). Alternatively, a kit can include multiple unit dosage forms of a low amount of PA. For example, each of the multiple unit dosage forms would contain a low amount of PA in a separate individual container (e.g., each unit dose of PA would be from less than 1 µg to 1 pG per dose). Kit components can be in a mixture of one or more containers and all of the various containers can be within single or multiple packages.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a lymphocyte" includes a plurality of such cells.

A number of embodiments of the invention have been described. Nevertheless, it will be understood that various modifications may be made without departing from the spirit and scope of the invention. Accordingly, the following examples are intended to illustrate but not limit the scope of invention described in the claims.

Example 1

This example describes an animal inflammation (arthritis) model and histological data indicating that PA administered at very low concentrations can reduce inflammation and inhibit or reverse tissue damage caused by inflammation.

Three separate studies with three groups of five animals each (a total of 15 animals per treatment group). The first group is control, injected with phosphate buffered saline) PBS carrier. The second group received 100 μg Enbrel per mouse per day. This was the optimal Enbrel dose as described by the manufacturer (Immunex, Corp., Seattle, Wash.). The third group was injected with 10 picograms (pG) of PA in PBS carrier on Monday, Wednesday, and Friday during the treatment period (Amersham/Pharmacia Biotech, Piscataway, N.J.). PA may also be obtained from Sigma-Aldrich, St. Louis, Mo.; Pierce Chemical Co., Pittsburgh, Pa.; and Calbiochem, San Diego, Calif.

Table 1 below summarizes the clinical index data for the control group indicating a progressive inflammatory response in these susceptible animals. The response does not peak or plateau within the time limits used and control animals were sacrificed when the response jeopardized their health status.

TABLE 1

Control Clinical Index Reading -CIA Model

| Mean | S.D. | SEM | N | Day |
|---|---|---|---|---|
| 0 | 0 | 0 | 0 | 0 |
| 0 | 0 | 0 | 30 | 1 |
| 0.00 | 0.00 | 0.00 | 5.00 | 2 |
| 0.00 | 0.00 | 0.00 | 25.00 | 3 |
| 0.25 | 0.50 | 0.25 | 4.00 | 4 |
| 0.08 | 0.28 | 0.06 | 25.00 | 5 |
| 1.00 | 0.94 | 0.30 | 10.00 | 7 |
| 0.96 | 1.06 | 0.21 | 25.00 | 8 |
| 1.60 | 1.51 | 0.48 | 10.00 | 9 |
| 1.40 | 1.35 | 0.30 | 20.00 | 10 |
| 3.52 | 3.44 | 0.69 | 25.00 | 15 |
| 7.80 | 5.63 | 2.52 | 5.00 | 16 |
| 10.80 | 3.11 | 1.39 | 5.00 | 18 |
| 2.25 | 1.59 | 0.35 | 20.00 | 19 |
| 2.58 | 1.50 | 0.34 | 19.00 | 23 |

Table 1: Raw data of mean clinical index measurements for 15 control animals treated by the CIA protocol. This data is pooled data from 3 separate studies.

Table 2 shows similar data for the caliper measurements of the paws of the control group animals during the same time period. These data mirror the clinical index data with the exception that a plateau in the response appears after day 10. This response plateau corresponds with the kinetics of typical antibody induced inflammatory responses.

TABLE 2

Control Paw Measurement - CIA Model

| Mean | S.D. | SEM | N | |
|---|---|---|---|---|
| 165.80 | 9.31 | 2.08 | 20.00 | 0 |
| 164.95 | 11.91 | 1.52 | 61.00 | 1 |
| 168.50 | 6.13 | 1.37 | 20.00 | 2 |
| 168.50 | 8.90 | 1.41 | 40.00 | 3 |
| 172.30 | 4.75 | 1.06 | 20.00 | 4 |
| 171.38 | 7.26 | 1.15 | 40.00 | 5 |
| 167.00 | 16.12 | 2.55 | 40.00 | 7 |
| 182.35 | 19.06 | 3.01 | 40.00 | 8 |
| 176.44 | 19.56 | 3.05 | 41.00 | 9 |
| 207.45 | 36.93 | 8.26 | 20.00 | 10 |
| 212.28 | 38.03 | 6.01 | 40.00 | 15 |
| 204.30 | 31.25 | 6.99 | 20.00 | 16 |
| 212.95 | 36.18 | 8.09 | 20.00 | 18 |
| 217.40 | 44.90 | 10.04 | 20.00 | 19 |
| 224.30 | 44.01 | 9.84 | 20.00 | 23 |

Table 2: Raw data of mean caliper paw measurements for 15 control animals treated by the CIA protocol. This data is pooled data from 3 separate studies.

Histological analysis of knee and ankle of a control animal taken on day 15 of the inflammatory response indicated extensive immune infiltration and tissue destruction. Immunocytes accumulated in the synovium of control animal. Enbrel treated animals at day 35 showed continued immune infiltration in the synovium of knee and ankle and evidence of continued tissue destruction.

Table 3 summarizes the histological examination results of the knee and ankle joints of control, untreated DBA/1 animals. These ratings are assigned on a blinded basis by the histologist on a continuous scale from 1 to 10 with 1 representing a "normal" histological appearance and 10 a high degree of damage. Knee and ankle joints of the control animals after collagen induction show maximal tissue damage ("10"s). This correlates with both the Clinical index (Table 1) and physical measurement data (Table 2).

TABLE 3

Histology Rating of CIA Model - Control Animals

| Tissue | Histology Rating | N |
|---|---|---|
| Ankle | 10 | 15 |
| Knee | 10 | 15 |

PA treated animals at day 35 of the inflammatory response showed much less evidence of immune infiltration and only slight evidence of tissue destruction. Only a few host immunocytes were present in the synovium and there was no evidence of tissue fragments or tissue destruction. These data therefore demonstrate that PA reduces acute inflammation in the CIA model. These data also demonstrate that PA reduces tissue damage or promotes tissue repair more than Enbrel.

Tables 4 and 5 show the results of 3 separate studies testing the effect of PA (10 pG/injection, M/W/F). Enbrel was tested for comparison; the results obtained were comparable with published results. PA treatment was very effective, reaching significance at approximately 10% of the number of animals required for the Enbrel standard. The results for the total clinical index (Table 4) and the physical measurements (Table 5) are comparable.

TABLE 4

PA Treatment on the CIA model (Total Clinical Index)

| Treatment | Pooled Data: Day | Mean | C.I. N | P[1-tail] |
|---|---|---|---|---|
| Control | 15 | 3.52 | 25 | |
| | 17 | 3.88 | 25 | |
| | 19 | 2.25 | 20 | |
| Protein-A | 15 | 1.92 | 25 | 0.03 |
| | 17 | 1.95 | 24 | 0.02 |
| | 19 | 1.40 | 20 | 0.04 |
| Enbrel | 15 | 2.79 | 24 | 0.17 |
| | 17 | 3.41 | 24 | 0.30 |
| | 19 | 2.85 | 20 | 0.11 |

TABLE 5

PA Treatment on the CIA model (Measurement)

| Treatment | Pooled Data: Day | Mean | Meas. N | P[1-tail] |
|---|---|---|---|---|
| Control | 15 | 212.3 | 40 | |
| | 17 | 218.1 | 40 | |
| | 19 | 217.4 | 20 | |
| Protein-A | 15 | 195.4 | 36 | 0.02 |
| | 17 | 191.4 | 36 | 0.001 |
| | 19 | 197.2 | 20 | 0.05 |
| Enbrel | 15 | 204.2 | 36 | 0.18 |
| | 17 | 209.1 | 36 | 0.18 |
| | 19 | 230.3 | 20 | 0.19 |

Table 6 shows the results of a histological assessment of DBA/1 mice sacrificed at 1, 2 and 3 weeks during their treatment regimen. Both PA and Enbrel treatments show significant damage at the tissue level. These data demonstrate that in spite of the significant decreases in Total clinical index and paw measurements (Tables 4 and 5) there is still damage at the tissue level. PA treatment appears to delay tissue damage (treatment week one versus control) but does not prevent the damage.

TABLE 6

PA treatment and histological damage

| | Control | PA | Enbrel |
|---|---|---|---|
| 1 wk | Ankle: 10 | Ankle: 8 | Ankle: 1-5 |
| | Knee: 10 | Knee: 0-5 | Knee: 0-10 |
| 2 wk | Ankle: 10 | Ankle: 10 | Ankle: 10 |
| | Knee: 10 | Knee: 10 | Knee: 10 |
| 3 wk | Ankle: 10 | Ankle: 10 | Ankle: 10 |
| | Knee: 10 | Knee: 10 | Knee: 10 |

DBA/1 mice induced with Type II Collagen as per the CIA model protocol were treated immediately after the second antigen injection—solvent carrier (PBS) for the control, PA (at 10 pG per injection M/W/F), and Enbrel (100 ug/injection every day).

Table 7 shows histological results after extending treatment to 35 days. Control mice were sacrificed at 18 days for humanitarian reasons and their 18 day data are included for comparison. Enbrel treatment showed no amelioration of the histological damage. In contrast, PA treatment reversed histological damage at 14-21 days. This histological data correlates with the Total Clinical Index of these animals. Thus, PA treatment significantly reduced the severity of the acute inflammatory response and continuing treatment reversed the existing tissue damage caused by the response.

TABLE 7

PA extended Treatment and Histological assessment

| | Control @ 18 Days | PA @ 35 Days | Enbrel @ 35 Days |
|---|---|---|---|
| rating | Ankle: 10 | Ankle: 0-1 | Ankle: 10 |
| | Knee: 10 | Knee: 0-1 | Knee: 10 |

The histological assessment of these tissues included low, medium, and high magnification assessment. In both control (at 18 days, time of sacrifice) and Enbrel treatment groups the synovium had large numbers of activated lymphocytes, whereas the PA group at day 35 of treatment had few small lymphoid cells which were similar in number and morphology to those in the DBA/1 animals prior to Type II collagen antigen induction.

In sum, these data demonstrate that paw measurements and the clinical index assessments document the induced inflammatory response in the CIA animal model; that PA reduces the inflammatory response during the acute phase (P values vs control <0.05) and reverses the histological damage caused by the response by day 35 of treatment; that PA has its ameliorative effect at concentrations and dosing schedules predicted by the BXSB animal model and Tissue Culture assessments (discussed further below); and that Enbrel does reduce inflammation on Day 14 (not significantly with N=15) but does not reduce inflammatory damage observed at day 35, indicating that PA is more effective than Enbrel.

Example 2

This example describes data indicating that the mechanism of action (MOA) of PA appears distinct from Enbrel.

The accepted MOA for the CIA animal model is competitive inhibition of the expression of α-TNF. Enbrel is a known α-TNF inhibitor. Regression analysis of the Enbrel data indicated a delay in the onset of the inflammatory response. In contrast, regression analysis of the PA data suggested an alteration in the inflammatory process itself. The MOA of PA therefore does not appear to be primarily through α-TNF inhibition. In addition, PA is not only more effective than Enbrel in reducing the induced inflammatory response in treated animals but is also capable of reversing pre-existing tissue damage caused by that response.

While not being bound by any theory, PA may therefore "modulate" a basal control mechanism responsible for integrating immune-dependent responses. This MOA would encompass α-TNF inhibition but from a self-regulatory perspective instead of simple target molecule competitive inhibition. Such a MOA is predicted to have the following properties:

1) small amounts required—a regulatory effect on a primitive control mechanism that "branches" to influence additional mechanisms;

2) self-regulatory—if PA acts at an early control point then the system will have the ability to regulate the intensity and direction of the mechanism resulting in few if any side effects;

3) pleiotropic target i.e. non-cell-lineage specific—if PA control point is early then the subsequent control should be diverse, and the concentration of PA and dosing schedule should be constant; and 4) PA effector molecule structure should be found in association with a number of more complex structures.

Example 3

This example describes data indicating that PA has multiple modulatory activities in an animal model characterized by a combined autoimmune deficiency disease having a genetic basis resulting in early death. In particular, PA prevents early onset of wasting, expansion of the splenic compartment, regulates humoral immunity (autoantibodies), cellular immunity ($TH_1/TH_2$ balance) and lymphoid cell differentiation as well as ameliorating tissue damage caused by the disease processes.

The BXSB murine model is a gene (Yaa) based animal model that manifests with early death in males, typically from kidney failure. This model is considered in the literature as an analog for human systemic lupus. The gene defect expresses as a series of inter-related progressive systemic autoimmune diseases having the following pattern: thymic atrophy, antinuclear antibody, liver disease, arthritic disease, kidney disease and early death.

Because this is a genetic model with multiple outcomes previous studies by other investigators have concentrated on single aspects of the disease. The effect of PA on multiple aspects of the disease process studied herein include:
1. overall effect on the animal's physiology
   a. growth curves
   b. histology of thymus, liver, brain, kidney, ankle, and knee
2. immune regulation—cellular proliferation/apoptosis
   a. splenic size, and
   b. cell count
3. lymphocyte dynamics
   a. T/B responses to mitogenic stimuli
4. lymphocyte function
   a. Humoral immunity
      i. Ig-PFC production
      ii. Auto-antibody: ANA, anticardiolipin
   b. Cellular Immunity
      i. Natural killer
   c. Cell surface markers
   d. Cellular cytokines Study design:
1. Chronic Treatment, Abnormal: groups of 25 male BXSB (control+4 treatment groups) were treated with PA on M/W/F over a 15 week period with periodic peel-off sacrifices (usually every 3 weeks of treatment)
2. Chronic Treatment, Normal: groups of 15 male C57BL/6J were treated with PA on M/W/F over a 15 week period with periodic peel-off sacrifices (usually every 3 weeks of treatment)
3. Acute Treatment, Abnormal: groups of 15 male BXSB were treated for 3 weeks with amounts of PA determined above, and then animals were sacrificed 3.6 and 9 weeks post treatment.
4. Acute Treatment, Normal: groups of 15 male C57BL/6J were treated for 3 weeks with amounts of PA determined above, and then animals were sacrificed 3.6 and 9 weeks post treatment.

Determination of PA Concentration:

PA amounts were administered to BXSB over eight logs of concentration, from 1 µG/injection to $10^{-7}$ µG/injection. The results indicate two PA optima, one at 0.01 µG/injection and another at $10^{-5}$ µG/injection. The shape of the dose-response curves is Gaussian. For the sake of clarity the data presented is for $10^{-5}$ µG/injection (FIG. 1).

FIG. 1 shows the weight gain of BXSB males following PA administration. The weights were taken each time the animals were injected with either carrier or PA. Panel A is the weight gain growth curve for a normal C57BL/6J mouse strain, and is presented to show the typical shape of a normal weight gain growth curve. Panel B shows the cumulative sum of weight gain data from 25 control BXSB male mice. This curve shows a weight peak at approximately 4 months of age followed by a decrease in body weight, which corresponds to the reported onset of the BSXB autoimmune disease. The decrease in body weight leads to the "wasting" syndrome linked to immune complex deposition in the kidney.

Panel C shows the effect of chronic administration of PA at the optimal two concentrations (8 concentrations studied). Both the 0.01 µG/injection and 0.00001 µG/injection show significant changes in both the shape of the weight gain growth curve comparing better with the normal logistic shape than with the BXSB control and the average weight of both the treated animal groups is significantly higher than control (X=24.16 P=0.0002, for the $10^{-5}$ µG dose).

In order to analyze these growth curves and compare them when treating groups of BXSB animals with PA a regression analysis was performed on the data. The C57BL/6J growth data presented above, is best represented by the following cubic equation:

$$C57BL/6J\ Control\text{-}y = -0.0286x^3 + 0.4067x^2 - 0.8452x + 16.816\ [R^2 = 0.9886]$$

The R-squared value indicates an extremely good fit between the actual data and the line equation. The equation itself is a relatively simple extraction of a "logistic" shaped curve, which is typical of normal growth curves (FIG. 1).

There are four separate data sets for the control BXSB growth curve. All data sets agree internally and the overall equation for the pooled data is as follows:

$$Pooled\ BXSB\text{-}y = -0.0001x^3 + 0.0034x^2 + 0.1851x + 18.746\ [R^2 = 0.9384]$$

This equation is a quantitative representation of the differences in curve shape noted between FIG. 1, panels A and B. The cubic and quadratic function define the overall shape and the very low values define the rate of increase in weight and the "wasting" phase where the weights are seen to decrease as a function of time. In this study the aim is not to make the BXSB growth curve "look like" the C57BL/6J curve, as each strain has there own specific growth characteristics, but rather to increase the rate of growth initially and decrease or eliminate the "wasting phase" evident in FIG. 1, panel D.

Table 8 shows the fitted equations for the various PA treatment groups of BXSB animals. The slope of the initial growth curve, which indicates growth rate, is severely restricted in BXSB control animals. The inflexion point in BXSB control animals indicates the lethal effect of the disease process. The results indicate that PA treatment has a positive effect on both growth rate and lethality in a dose dependent manner.

TABLE 8

PA effect on the growth kinetics of BXSB

| Treatment | Growth equation |
| --- | --- |
| Pooled BXSB | y = −0.0001x3 + 0.0034x2 + 0.1851x + 18.746 |
| | R2 = 0.9384 |
| Rx 1.0 PA | y = 4E−06x3 − 0.4942x2 + 18171x − 2E+08 |
| | R2 = 0.9087 |
| Rx 0.1 PA | y = −1E−04x3 + 10.697x2 − 392306x + 5E+09 |
| | R2 = 0.9463 |
| Rx 0.01 PA | y = 3E−05x3 − 2.8056x2 + 102980x − 1E+09 |
| | R2 = 0.918 |
| Rx 0.001 PA | y = 1E−05x3 − 1.3946x2 + 51161x − 6E+08 |
| | R2 = 0.9773 |
| Rx 0.0001 PA | y = −4E−05x3 + 4.2053x2 − 154454x + 2E+09 |
| | R2 = 0.9487 |
| Rx 0.00001 PA | y = −1E−05x3 + 1.4883x2 − 54653x + 7E+08 |
| | R2 = 0.8665 |
| Rx 0.000001 PA | y = 3E−05x3 − 2.9251x2 + 107455x − 1E+09 |
| | R2 = 0.8682 |
| Rx 0.0000001 PA | y = −5E−06x3 + 0.5628x2 − 20666x + 3E+08 |
| | R2 = 0.9474 |

Histological Analysis:

The histological deterioration of various organs of the BXSB mouse model is the hallmark of a combined autoimmune deficiency disease. This syndrome is multi-facetted and involves a number of organs. The organ damage is progressive and individual damage may vary according to tissue type.

Table 9 shows the results from the histological analysis of higher amounts of PA (1 to 0.001 μg/injection) and indicates that PA changed the onset and/or severity of the histological changes in a dose dependent manner. Table 10 shows similar data for lower amounts of PA (0.00001 to 0.0000001 μg/injection). Both PA doses exhibited the greatest improvement in organ histology.

Tables 9 and 10: Histology of BXSB autoimmune disease processes in tissues including thymus, liver, kidney, knee and ankle.

Example 4

This example describes data indicating that PA has immune modulatory activity (e.g., proliferation, apoptosis or differentiation) in spleen reflected by inhibition of splenic expansion and splenocyte cell numbers.

Spleens were removed from animals during the studies. Normal C57BL/6J spleen was a reference point. Spleens from untreated BXSB animals were significantly enlarged. In contrast, PA treated BXSB animal spleens resembled the size of normal C57BL/6J spleen.

| Tissue | BXSB Control | Rx 1 μg PA | Rx 0.1 μg PA | Rx 0.01 μg PA | Rx 0.001 μg PA |
|---|---|---|---|---|---|
| Thymus | 4+ (10-20 wks) | 4+ (16-20 wks) | 4+ (10-20 wks) | 4+ (16-20 wks) | 4+ (12-13 wks) |
| Liver (double nuclei) | local inflammation 20 wks | N/A | local inflammation 19 wks | local inflammation 10 wks | local inflammation 20 wks |
| Kidney | normal | normal | normal | normal | normal |
| Knee | normal | normal | normal | inflammation 16 wks | normal |
| Ankle | fibers disintegrating 20 wks | inflammation 19 wks | inflammation 10 wks | inflammation 16 wks | normal |

| Tissue | BXSB Control | Rx 0.0001 μg PA | Rx 0.00001 μg PA | Rx 0.000001 μg PA | Rx 0.0000001 μg PA |
|---|---|---|---|---|---|
| Thymus | 4+ (11-22 wks) | normal | 4+ (11-22 wks) | 4+ (22 wks) | 4+ (22 wks) |
| Liver (double nuclei) | local inflammation 20 wks | normal | local inflammation 19 wks | normal | local inflammation 11 wks |
| Kidney | normal | normal | normal | normal | normal |
| Knee | normal | normal | normal | normal | normal |
| Ankle | normal | normal | normal | normal | normal |

The results in Tables 9 and 10 indicate that PA treatment of BXSB mice was able to decrease autoimmune damage in a dose dependent fashion. Treatment delayed the onset of thymic atrophy, and reduced the severity of liver and joint inflammation. The kidneys remained with in normal range. The tissues of PA treated animals exhibited a reversal of the damage present in BXSB control tissues, although they were not completely normal as compared to C57BL/6J animals. The optimal PA dose was 0.0001 μg, which is consistent with other assay systems (e.g., Ig-PFC production, NK activity, mitogen response pattern, cytokine production, autoantibody production, spleen size, histological improvements).

In sum, the studies indicate that PA prevents the early onset of wasting, and ameliorates or reverses damage caused by The enlarged spleens in untreated BXSB animals is known as splenomegalia, and is the result of either a massive systemic infection process or of aberrant cellular apoptosis or proliferation. Because these animals are maintained in a sterile environment the enlarged spleen is likely the result of faulty cell growth/death control. Another explanation for enlarged spleen would be that the cells had increased in their individual size, a process known as blastosis. Examination of the fluorescently activated cell sorting (FACS) data to measure cell size ruled out this possibility. FACS analysis revealed that although a trend to slightly larger cells was observed in the BXSB controls, no statistically significant increase in cell size was observed. Consistent with these findings is that BXSB splenocyte numbers are more than five-times those of normal animals (Table 11, top).

TABLE 11

| | PA Effect on Splenomegalia | | |
|---|---|---|---|
| | BXSB control | C57BL/6J | DBA/2J |
| MEAN | 5.E+08 | 9.E+07 | 1.E+08 |
| SEM | 4.E+07 | 7.E+06 | 6.E+06 |
| N | 20 | 20 | 20 |

TABLE 11-continued

PA Effect on Splenomegalia

| | Rx 1.0 PA | P-value | Rx 0.1 PA | P-value | Rx 0.01 PA | P-value | Rx 0.001 PA | P-value |
|---|---|---|---|---|---|---|---|---|
| MEAN | 1.E+08 | 8.68E−03 | 1.E+08 | 7.32E−04 | 7.E+07 | 1.02E−06 | 1.E+08 | 8.92E−06 |
| SEM | 7.E+07 | | 5.E+07 | | 4.E+07 | | 4.E+07 | |
| N | 3 | | 3 | | 5 | | 4 | |

| | Rx E-04 PA | P-value | Rx E-05 PA | P-value | Rx E-06 PA | P-value | Rx E-07 PA | P-value |
|---|---|---|---|---|---|---|---|---|
| MEAN | 3.E+08 | 1.73E−02 | 1.E+08 | 6.70E−05 | 3.E+08 | 9.54E−02 | 2.E+08 | 7.26E−05 |
| SEM | 6.E+07 | | 3.E+07 | | 1.E+08 | | 4.E+07 | |
| N | 4 | | 3 | | 4 | | 5 | |

Table 11 (top) shows the contents of the spleens of both control mouse strains, C57BL/6J and DBA/2J, and BXSB males. BXSB splenocyte cell numbers are more than 5 times those found for either of the normal strains. PA treatment significantly reduced BXSB splenocyte numbers (Table 11, bottom).

In sum, the studies indicate that PA regulates expansion of the spleenic compartment (proliferation/apoptosis) caused by the autoimmune disease and splenocyte numbers. PA treatment both reduced spleen size and splenocyte numbers significantly in a dose dependent fashion.

Example 5

This example describes data indicating that BXSB animals exhibit aberrant splenocyte differentiation or proliferation or apoptosis. This data therefore indicates that PA activity in BXSB spleen includes re-regulating aberrant/deficient splenocyte differentiation or splenocyte proliferation/apoptosis (i.e. restoring normal cell proliferation or apoptosis).

Mitogens are lectins that have the non-specific capacity to stimulate cellular division in general populations of cells (e.g., T and/or B lymphocytes). Lectins are found in plants and animals and are best characterized as precursors to modern day antibody molecules. Lectins are used for intracellular and other forms of communication.

To determine whether the T-lymphocyte compartment in BXSB mice is aberrant, two T-cell specific and two B-cell specific mitogens were used to study the response of splenocytes isolated from BXSB mice. 7 different mitogen concentrations and 4 kinetic time points were used to test BXSB animals' splenocyte response in terms of the response amplitude (an indication of the number of cells present), and secondly, the optimal stimulation concentration (an indication of the differentiation status of the cells).

In brief, BXSB and control mice were sacrificed periodically during the treatment regimen and their spleens removed. Splenocyte cell suspensions at 1 to $2 \times 10^6$/ml are dispensed into 96 well plates. Mitogens (10 μG/10 uL to 0.01 μG/10 uL) were added in triplicate to the wells and the cultures harvested at 24 hour intervals from 24 to 96 hours of culture. All cultures were treated with tritiated thymidine for 16 hours prior to harvest. The DNA, including the newly synthesized radiolabeled DNA, is extracted on glass fiber filters and the radioactivity determined by liquid scintillation counting.

TABLE 12

Normal (C57BL/6) mitogen responses (Stimulation Index, S.I.)

| | 10.00 | 5.00 | 1.00 | 0.50 | 0.10 | 0.05 | 0.01 |
|---|---|---|---|---|---|---|---|
| PHA: SI | | | | | | | |
| MEAN | 24.56 | 29.54 | 33.39 | 19.95 | 3.07 | 1.79 | 1.03 |
| S.D. | 11.39 | 13.47 | 14.00 | 11.47 | 3.40 | 1.69 | 0.57 |
| SEM | 2.15 | 2.55 | 2.65 | 2.17 | 0.64 | 0.32 | 0.11 |
| Count | 27 | 27 | 27 | 27 | 27 | 27 | 27 |
| Con-A: SI | | | | | | | |
| MEAN | 0.57 | 1.69 | 48.07 | 11.79 | 1.83 | 2.00 | 2.39 |
| S.D. | 0.27 | 1.50 | 32.63 | 15.80 | 1.94 | 1.08 | 2.99 |
| SEM | 0.05 | 0.28 | 6.17 | 2.99 | 0.37 | 0.20 | 0.56 |
| Count | 27 | 27 | 27 | 27 | 27 | 27 | 27 |
| SEB: SI | | | | | | | |
| MEAN | 18.70 | 15.79 | 10.61 | 7.87 | 5.23 | 3.41 | 1.47 |
| S.D. | 11.49 | 8.69 | 6.14 | 5.57 | 4.57 | 2.47 | 0.55 |
| SEM | 2.17 | 1.64 | 1.16 | 1.05 | 0.86 | 0.47 | 0.10 |
| Count | 27 | 27 | 27 | 27 | 27 | 27 | 27 |
| LPS: SI | | | | | | | |
| MEAN | 105.66 | 103.65 | 94.60 | 85.92 | 69.95 | 59.05 | 39.44 |
| S.D. | 46.55 | 46.89 | 46.30 | 52.67 | 41.29 | 36.17 | 29.92 |
| SEM | 8.80 | 8.86 | 8.75 | 9.95 | 7.80 | 6.84 | 5.66 |
| Count | 27.00 | 27.00 | 27.00 | 27.00 | 27.00 | 27.00 | 27.00 |

Table 12 shows the mitogen responses of C57BL/6J mice to phytohemaglutinin (PHA), concanavalin A (Con-A), staphylococal enterotoxin B (SEB), and lipopolysaccharide (LPS). PHA and Con-A stimulate basic T lymphocyte populations to proliferate in a dose dependent fashion, whereas SEB, and LPS stimulate the dose dependent proliferation of B-lymphocyte populations.

TABLE 13

BXSB mitogen responses

| | 10.00 | 5.00 | 1.00 | 0.50 | 0.10 | 0.05 | 0.01 |
|---|---|---|---|---|---|---|---|
| PHA: SI | | | | | | | |
| Mean | 4.63 | 2.17 | 3.64 | 4.29 | 3.77 | 2.55 | 1.95 |
| S.D. | 6.29 | 1.40 | 1.56 | 2.11 | 1.76 | 0.81 | 0.88 |
| SEM | 0.87 | 0.19 | 0.22 | 0.29 | 0.24 | 0.11 | 0.12 |
| N | 39 | 39 | 39 | 39 | 39 | 39 | 39 |
| Con-A: SI | | | | | | | |
| Mean | 0.99 | 2.42 | 6.34 | 7.08 | 3.93 | 1.88 | 1.67 |
| S.D. | 1.02 | 2.07 | 4.32 | 3.69 | 3.46 | 0.97 | 0.93 |
| SEM | 0.14 | 0.29 | 0.60 | 0.51 | 0.48 | 0.14 | 0.13 |
| N | 39 | 39 | 39 | 39 | 39 | 39 | 39 |

TABLE 13-continued

BXSB mitogen responses

|  | 10.00 | 5.00 | 1.00 | 0.50 | 0.10 | 0.05 | 0.01 |
|---|---|---|---|---|---|---|---|
| SEB: SI |  |  |  |  |  |  |  |
| Mean | 6.05 | 6.10 | 5.21 | 4.70 | 3.00 | 2.53 | 1.91 |
| S.D. | 3.77 | 3.18 | 2.69 | 3.48 | 1.66 | 1.85 | 1.04 |
| SEM | 0.52 | 0.44 | 0.37 | 0.48 | 0.23 | 0.26 | 0.14 |
| n | 39 | 39 | 39 | 39 | 39 | 39 | 39 |
| LPS: SI |  |  |  |  |  |  |  |
| Mean | 26.40 | 27.76 | 29.58 | 24.83 | 10.85 | 7.08 | 3.97 |
| S.D. | 18.99 | 20.58 | 20.78 | 14.66 | 5.50 | 3.76 | 1.64 |
| SEM | 2.63 | 2.85 | 2.88 | 2.03 | 0.76 | 0.52 | 0.23 |
| N | 39 | 39 | 39 | 39 | 39 | 39 | 39 |

Table 13 shows the results from the mitogen study of BXSB control. Statistical analyses indicates that all mitogen responses are significantly lower than C57BL/6J control. In addition, the shape of the PHA and Con-A response curves for BXSB control are different from normal C57BL/6J control. For both there was a shift to lower mitogen concentrations to achieve a peak response. These changes in response curve shape have been associated with changes in differentiation status.

TABLE 14

Statistical Comparison of BXSB Mitogen Responses to Control

|  | 10.00 | 5.00 | 1.00 | 0.50 | 0.10 | 0.05 | 0.01 |
|---|---|---|---|---|---|---|---|
| PHA | 1.E−10 | 2.E−11 | 2.E−11 | 5.E−07 | 5.E−02 | N.S. | N.S. |
| Con-A | N.S. | N.S. | 6.E−07 | 6.E−02 | N.S. | N.S. | N.S. |
| SEB | 2.E−05 | 4.E−06 | 4.E−05 | 2.E−04 | 6.E−04 | 1.E−03 | N.S. |
| LPS | 5.E−09 | 2.E−08 | 5.E−07 | 5.E−06 | 8.E−08 | 8.E−08 | N.S. |

Table 14 shows a statistical comparison of control BXSB. Mitogen responses to control C57BL/6. In almost every case, the amplitude of the mitogen response in BXSB is suppressed indicating a diminution of the mature cell population and a shift in the optimal response concentration to a lower value. These data therefore indicate aberrant differentiation in control BXSB splenocytes which leads to over-proliferation or decreased apoptosis of splenocytes.

TABLE 15

PHA Response as a Function of PA treatment

| PHA: S.I. | 10.00 | 5.00 | 1.00 | 0.50 | 0.10 | 0.05 | 0.01 |
|---|---|---|---|---|---|---|---|
| 1 PA | 2.23 | 3.27 | 8.64 | 11.52 | 10.91 | 4.63 | 1.86 |
| 0.1 PA | 1.08 | 1.82 | 4.13 | 5.25 | 4.76 | 2.95 | 2.62 |
| 0.001 PA | 1.52 | 1.21 | 2.70 | 4.41 | 3.90 | 2.57 | 1.94 |
| 0.0001 PA | 5.53 | 4.03 | 9.65 | 15.41 | 10.91 | 3.91 | 1.95 |
| 1E−04 PA | 5.71 | 2.98 | 5.14 | 6.82 | 6.22 | 2.73 | 1.66 |
| 1E−05 PA | 7.73 | 7.00 | 8.34 | 9.80 | 7.26 | 3.47 | 1.89 |
| 1E−06 PA | 2.70 | 3.13 | 4.47 | 4.82 | 3.84 | 3.29 | 2.20 |
| 1E−07 PA | 5.08 | 5.84 | 3.41 | 4.22 | 3.90 | 2.37 | 2.00 |

TABLE 16

Con-A Response as a Function of PA treatment

| Con-A: S.I. | 10.00 | 5.00 | 1.00 | 0.50 | 0.10 | 0.05 | 0.01 |
|---|---|---|---|---|---|---|---|
| 1 PA | 1.42 | 4.88 | 23.61 | 36.83 | 6.57 | 2.70 | 2.07 |
| 0.1 PA | 1.29 | 5.43 | 8.51 | 8.06 | 2.00 | 2.20 | 1.64 |
| 0.001 PA | 1.34 | 3.31 | 8.26 | 17.4 | 9.14 | 3.33 | 1.92 |

TABLE 16-continued

Con-A Response as a Function of PA treatment

| Con-A: S.I. | 10.00 | 5.00 | 1.00 | 0.50 | 0.10 | 0.05 | 0.01 |
|---|---|---|---|---|---|---|---|
| 0.0001 PA | 1.92 | 2.05 | 27.27 | 51.59 | 10.40 | 2.10 | 2.02 |
| 1E−04 PA | 0.56 | 1.31 | 7.29 | 15.26 | 6.87 | 4.56 | 1.79 |
| 1E−05 PA | 0.76 | 3.10 | 5.31 | 14.29 | 7.69 | 2.25 | 1.34 |
| 1E−06 PA | 1.01 | 2.34 | 5.04 | 15.98 | 8.03 | 2.85 | 2.52 |
| 1E−07 PA | 1.65 | 2.90 | 9.05 | 22.83 | 8.10 | 2.17 | 2.05 |

TABLE 17

SEB Response as a Function of PA treatment

| SEB: S.I. | 10.00 | 5.00 | 1.00 | 0.50 | 0.10 | 0.05 | 0.01 |
|---|---|---|---|---|---|---|---|
| 1 PA | 13.39 | 11.88 | 12.41 | 8.39 | 6.42 | 4.73 | 3.76 |
| 0.1 PA | 6.25 | 6.57 | 4.29 | 4.15 | 2.37 | 1.68 | 1.32 |
| 0.001 PA | 7.51 | 7.54 | 10.06 | 7.37 | 5.76 | 5.28 | 3.82 |
| 0.0001 PA | 14.60 | 12.60 | 9.55 | 5.72 | 4.66 | 4.21 | 2.05 |
| 1E−04 PA | 8.01 | 5.15 | 6.48 | 4.55 | 5.12 | 2.97 | 1.34 |
| 1E−05 PA | 6.92 | 8.02 | 7.94 | 5.28 | 4.13 | 3.54 | 3.40 |
| 1E−06 PA | 9.34 | 8.01 | 9.74 | 5.82 | 4.33 | 5.73 | 4.20 |
| 1E−07 PA | 5.92 | 5.67 | 5.88 | 6.90 | 2.33 | 2.35 | 2.33 |

TABLE 18

LPS Response as a Function of PA treatment

| LPS: S.I. | 10.00 | 5.00 | 1.00 | 0.50 | 0.10 | 0.05 | 0.01 |
|---|---|---|---|---|---|---|---|
| 1 PA | 52.36 | 52.74 | 56.61 | 49.82 | 22.00 | 18.14 | 8.47 |
| 0.1 PA | 20.73 | 20.47 | 20.23 | 16.29 | 7.47 | 6.42 | 3.45 |
| 0.001 PA | 13.85 | 15.86 | 16.57 | 12.71 | 8.52 | 6.46 | 4.76 |
| 0.0001 PA | 37.85 | 42.85 | 41.46 | 37.76 | 19.10 | 15.78 | 6.41 |
| 1E−04 PA | 23.10 | 37.92 | 32.05 | 27.29 | 13.38 | 20.52 | 7.49 |
| 1E−05 PA | 27.43 | 27.18 | 27.90 | 28.69 | 17.44 | 16.69 | 8.88 |
| 1E−06 PA | 22.67 | 21.88 | 17.14 | 17.60 | 12.40 | 9.27 | 6.30 |
| 1E−07 PA | 14.49 | 16.56 | 17.95 | 18.56 | 10.99 | 7.20 | 3.40 |

Tables 15 to 18 show the effects of PA on the mitogen responses of BXSB splenocytes. Although the kinetics are complex several conclusions can be made. That PA (0.5 µG) elevates PHA and Con-A responses indicates normalization of T and B cell population dynamics. That PA also restores much of the amplitude of the mitogen responses and the shape of the response curves indicates a partial or complete restoration of T cell and B cell response to mitogens.

In sum, the studies indicate that the aberrant BXSB splenic lymphocyte numbers as well as typical T and B mitogen responses can be corrected, at least in part, with PA treatment.

Example 6

This example describes data indicating that PA reduces the amount of autoantibodies likely responsible for tissue destruction in BXSB animals.

Humoral immunity is responsible for antibody production and is significant as rheumatoid antibody are found in a significant percentage of RA patients. Abnormal antibodies have been found in the synovium of some patients. In the BXSB model, abnormal antibodies are produced.

Spleen cells obtained from control and PA treated BXSB animals were studied in a plaque forming cell (PFC) assay. In this assay the target red blood cells are labeled with protein-A which will bind any secreted immunoglobulin regardless of antigenic specificity thus providing a broad view of humoral immunity.

TABLE 19

BXSB Non-specific Antibody Producing Cells

|      | BXSB  | C57BL/6J |
|------|-------|----------|
| Mean | 60333 | 611.80   |
| S.D. | 33915 | 658.67   |
| N    | 45    | 75.00    |
| SEM  | 5056  | 120.26   |

Table 19 shows the Ig-PFC responses of control BXSB splenocytes, which is 100× greater than control C57BL/6 splenocytes indicating aberrant antibody production in the BXSB animals.

TABLE 20

PA Treatment and Ig-PFC Production in BXSB Animals

|          | BXSB Control | Rx 1 PA   | RX 0.1 PA | Rx 0.01 PA | Rx 0.001 PA |
|----------|--------------|-----------|-----------|------------|-------------|
| Mean     | 60333        | 20741     | 35808     | 27909      | 30533       |
| N        | 45           | 11        | 12        | 11         | 15          |
| S.E.M.   | 5056         | 6603      | 12010     | 2959       | 9581        |
| P-values |              | 4.22E−05  | 0.04      | 5.16E−07   | 0.01        |

|          | Rx 0.0001 PA | Rx 0.00001 PA | Rx 0.000001 PA | Rx 0.0000001 PA |
|----------|--------------|---------------|----------------|-----------------|
| Mean     | 3850         | 12310         | 16278          | 11042           |
| N        | 5            | 10            | 9              | 12              |
| S.E.M.   | 696          | 2040          | 4068           | 1751            |
| P-values | 7.33E−15     | 2.92E−12      | 3.11E−08       | 8.16E−13        |

Table 20 shows the dose related effect of PA on Ig-PFC production. All PA amounts significantly reduced the overproduction of Ig-PFCs with 0.0001 μG PA showing the greatest reduction.

BXSB control splenocytes make and secrete antibodies at enormous levels (61400+-6435 PFC/1E06). This is approximately 100 times the values observed in C57BL/6J normal controls. PA treatment significantly reduces auto-antibody levels in a dose and time dependent manner.

TABLE 21

PA and the Effect on Circulating Auto-antibodies in BXSB Animals

|         | Control | Rx 0.01 PA |
|---------|---------|------------|
| 2 weeks | 0.262   | 0.016      |
|         | 0.318   | 0.000      |
| 5 weeks | 0.272   | 0.029      |
|         | 0.360   | −0.032     |
| 11 weeks| 1.317   | 0.103      |
|         | 1.449   | 0.125      |
| 14 weeks| 0.402   | 0.283      |
|         | 0.357   | 0.206      |

Table 21 shows the development of auto-antibodies in BXSB animals (the higher numbers indicate greater amounts of circulating autoantibodies). PA treatment reduces autoantibody levels at all time points measured.

TABLE 22

The Effect of PA Concentration on Auto-antibody Production (ANA)

|         | Control | Rx 1 PA | Rx 0.1 PA | Rx 0.01 PA | Rx 0.001 PA |
|---------|---------|---------|-----------|------------|-------------|
| Mean    | 0.475   | 0.306   | 0.176     | 0.091      | 0.341       |
| N       | 11      | 7       | 7         | 9          | 11          |
| S.E.M   | 0.14    | 0.03    | 0.09      | 0.03       | 0.10        |
| P-value |         | 0.16    | 0.07      | 0.02       | 0.25        |

|         | Rx 0.0001 PA | Rx 0.00001 PA | Rx 0.000001 PA | Rx 0.0000001 PA |
|---------|--------------|---------------|----------------|-----------------|
| Mean    | 0.229        | 0.090         | 0.176          | 0.098           |
| N       | 9            | 12            | 12             | 15              |
| SEM     | 0.04         | 0.06          | 0.03           | 0.03            |
| P-value | 0.02         | 0.02          | 0.08           | 0.02            |

Table 22 shows that PA-mediated reduction of autoantibodies is dose dependent. The greatest reduction occurs at 0.00001 μG.

In sum, PA regulates the number of non-specific antibodies, reducing the amount of damaging autoantibodies. That PA also reduces antibody producing cells in BXSB spleens correlates with this data. Thus, PA treatment restores, at least in part, humoral immunity.

Example 7

This example describes data indicating that PA reduces cytotoxicity response of BXSB mice, re-regulating this response to at or near base-line levels.

The cellular component of the immune system is the primary integrator of function for the entire immune system, supplying the T-cells and B-cells in their various differentiated forms for both recognition and effector function. In the BXSB animal model there have been reports that the Cell Mediated Immune (CMI) system is intact. However, contrary to these reports the data described below indicate that CMI is affected in the BXSB mouse.

BXSB mice, both control and treated with PA, were studied for their ability to recognize and lyse non-specific targets labeled with radio-labeled chromium. In brief, about 200 μl spleen cells ($1 \times 10^7$/ml) from control and treated BXSB mice were plated on a microtiter plate in RPMI medium and five two fold serial dilutions were made in RPMI media. P815 cells were radiolabeled with chromium ($Cr^{51}$) and added to each well of a 96 well plate, centrifuged for 12 minutes and then incubated for 3-4 hours at 37° C. Cells were re-centrifuged and a 110 μl sample counted for $Cr^{51}$. A more detailed protocol is contained in Current Protocols in Immunology, 3.11, Assays for T cell Function.

TABLE 23

Cytotoxicity Response of BXSB and Normal Mice

| E/F Ratio | BXSB Control % Specific Lysis | S.D. | C57BL/6J % Specific Lysis | S.D. | BXSB Rx 3 weeks (acute) % Specific Lysis | S.D. |
|---|---|---|---|---|---|---|
| 100:1 | 122.0 | 5.0 | 2.0 | 0.1 | 5.43 | 4.1 |
| 50:1 | 95.1 | 9.4 | -1.2 | 0.5 | 4.94 | 4.4 |
| 25:1 | 93.8 | 10.3 | -1.5 | 0.6 | 3.94 | 3.3 |
| 12.5:1 | 85.4 | 8.3 | -1.3 | 0.5 | 3.04 | 3.1 |
| 6.25:1 | 50.5 | 35.1 | -1.2 | 0.2 | 2.84 | 3.0 |
| 3.13:1 | 5.3 | 5.3 | -2.5 | 0.3 | | |

Table 23 shows that normal mice (middle column) have a typical base line level of natural killer activity to the P-815 target labeled with $Cr^{51}$; the level is between 0 and 3% cytotoxicity at an effector target ratio of 100:1. The left column shows the cytotoxicity response of BXSB mice to the same target; the level of cytotoxicity is extremely high at over 50% at an effector/target ratio of 6:1. PA treatment of BXSB over a 3 to 15 week period (right column) reduced cytotoxicity to base line levels, i.e. 0-3% at E/T ratio of 100:1 without any regression analysis possible.

In sum, the studies indicate that PA treatment reduces the un-regulated BXSB cytotoxicity responses by a factor of 20, to at or near control base-line levels. Thus, PA treatment restores, at least in part, cellular immunity.

Example 8

This example describes data indicating that PA regulates expression of CD markers reflecting the regulation of cell differentiation, proliferation or apoptosis of cells of lymphoid lineage.

The expression of clustered determinants (CD markers) indicate the differentiation status of lymphoid cells. PA specifically regulates these markers. This regulation has direct correlations with the data described above.

TABLE 24A

CD Marker Profiles

| | 69+4− | 69+4+ | 69−4+ | 4+8− | 4+8+ | 4−8+ | 69+8− | 69+8+ | 69−8+ |
|---|---|---|---|---|---|---|---|---|---|
| BL6 control | 7.6 +− 1.4 | 7.6 +− 1.6 | 85 +− 2.9 | 74 +− 4.4 | 7.6 +− 1.7 | 18 +− 3.2 | 30 +− 2.3 | 5.0 +− 0.9 | 66 +− 2.7 |
| N | 23 | 23 | 23 | 23 | 23 | 23 | 23 | 23 | 23 |
| BXSB 2-10 | 20 +− 4.1 | 13 +− 1.5 | 68 +− 5.1 | 42 +− 7.7 | 8.5 +− 1.3 | 49 +− 6.9 | 22 +− 5.7 | 7.8 +− 1.5 | 71 +− 6.9 |
| P one-tail | 0.009 | 0.017 | 0.006 | 0.002 | 0.34 | 0.0008 | 0.11 | 0.07 | 0.25 |
| BXSB 11-15 | 44 +− 1.0 | 20 +− 1.3 | 36 +− 2.1 | 16 +− 1.3 | 14 +− 0.8 | 70 +− 1.1 | 23 +− 2.3 | 14 +− 0.7 | 64 +− 2.2 |
| P one-tail | 2.5E−12 | 4.8E−5 | 1.8E−9 | 1.7E−12 | 0.002 | 3.3E−14 | 0.03 | 1.7E−6 | 0.3 |

Table 24A shows data of a number of T-cell CD markers. Approximately 80% of normal splenocytes (BL6 control) are non-activated (CD69−) T-cells (CD69−, CD4+). This population decreases in both young (2-10 experimental weeks, and 10 to 18 weeks chronological age) and old (11-15 experimental weeks, and 19 to 23 weeks chronological age) BXSB animals. There is also a kinetic effect: the 11-15 week BXSB animals are much more severely compromised in terms of their T-cell markers than younger BXSB animals. This correlates to decreased cellular function and increased overall death rate.

TABLE 24B

| | CD Marker Profiles cont'd | | | | | |
|---|---|---|---|---|---|---|
| | 19+45− | 19+45+ | 19−45+ | 80+25− | 80+25+ | 80−25+ |
| C57BL/6J | 3 +− 0.6 | 80 +− 2 | 18 +− 3 | 70 +− 3 | 13 +− 1 | 18 +− 1 |
| BXSB 2-10 wks | 8 +− 4 | 60 +− 12 | 35 +− 11 | 65 +− 7 | 17 +− 2 | 18 +− 5 |
| P [one-tail] | N.S. | N.S. | N.S. | N.S. | N.S. | N.S. |
| BXSB 11-15 wks | 14 +− 7 | 64 +− 22 | 22 +− 15 | 61 +− 6 | 18 +− 2 | 21 +− 8 |
| P [one-tail] | N.S. | N.S. | N.S. | N.S. | N.S. | N.S. |

Table 24B shows data of a number of B-cell CD markers. The first set of three markers are indicative of resting B-cells (i.e. non-activated) and the last three represent activated B cells. These data show that the B-cell population is refractory to both the strain and the stage of the disease process in the BXSB mice. Thus, it appears that the primary cellular immune component of BXSB combined immunodeficiency disease process involves T-cells.

Graph 1 shows data from the effect of chronic treatment (from 3 to 15 weeks) of BXSB mice with varying concentrations of PA (1E-03 to 1E-07 μG of PA/injection). The first significant feature of this data is that treatment of BXSB mice with PA regulates the population of CD69−/CD4+ T-cells. The regulation is inter-related with the regulation of the other T-cell markers which is to be expected because one cell population acts on others in the series (and other cell series) in both feedback and feed forward mechanisms. There is also a PA dose response effect on cell populations, consistent with the response described above in the functional assays; there is a dose-time kinetic response as well. These data indicate that PA treatment does in fact regulate T cell differentiation.

Figure 2:
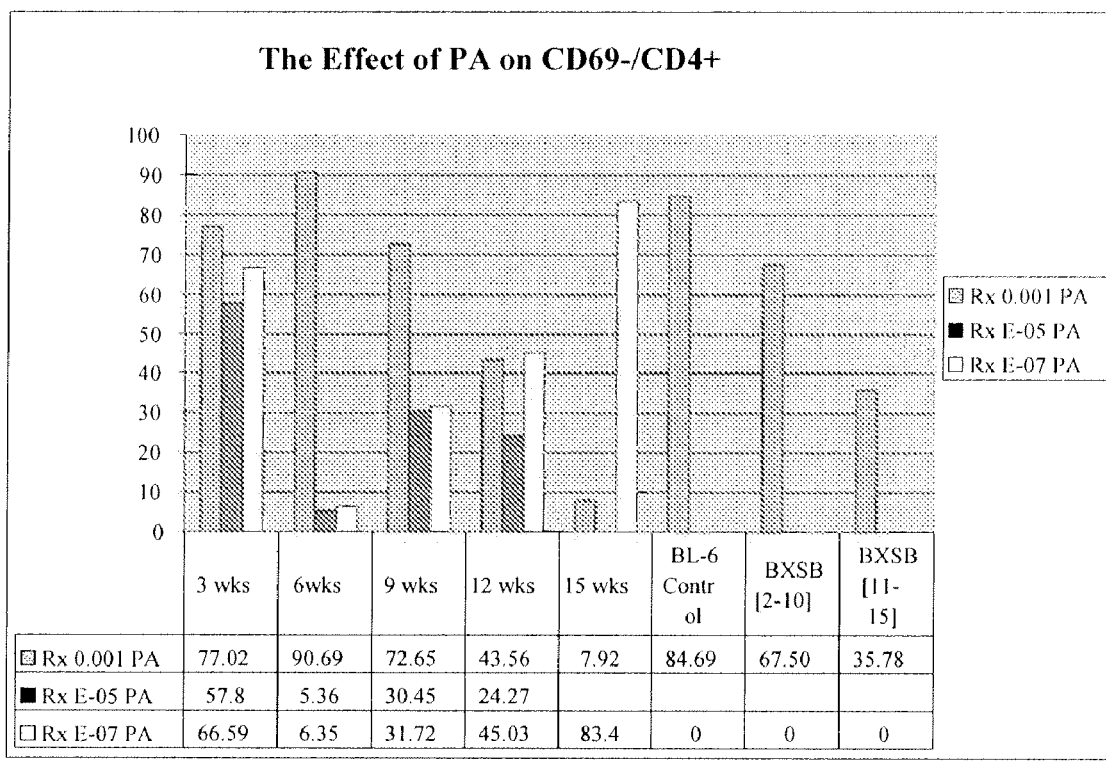

FIG. 2 also shows data indicating that the E-03 dose of PA rectifies the decrease in CD69−CD4+ observed in BXSB controls at early time points, although later losing this effect at longer time points of chronic treatment. In contrast, the E-07 dose appears to be effective at both short and long time points. These data are consistent with features of the Bio-Regulatory regimen: 1) The dose response curves are gaussian; and 2) the small amounts of PA that produce the effects suggest a process oriented target instead of a more traditional single effector target.

Table 25 shows the effect of chronic PA (1E-05 μG/dose) administered three times per week over a 6 and 9 week period compared with acute treatment at the same amount three times per week for a single 3 week period followed by an additional 6 and 9 weeks without treatment. The acute treatment is effective in modulating the CD marker display. Although complex the data demonstrate the inter-relationship between the various markers; again the CD 8 series appear to be lest sensitive to PA than the CD4 or B-cell series.

TABLE 25

Acute vs Chronic Treatment 0.00001 ug PA

| Percentage | CD69+CD4− | CD69+CD4+ | CD4+CD69− | CD4+CD8− | CD4+CD8+ | CD8+CD4− | CD69+CD8− | CD69+CD8+ | CD8+CD69− |
|---|---|---|---|---|---|---|---|---|---|
| BXSB Control | 19.73 | 12.45 | 67.50 | 41.85 | 8.48 | 49.24 | 21.53 | 7.80 | 70.67 |
| 6 wks acute | 56.25 | 22.42 | 21.34 | 17.64 | 7.68 | 73.59 | 24.91 | 5.56 | 69.54 |
| 9 wks Acute | 63.37 | 18.82 | 17.81 | 24.38 | 12.81 | 61.90 | 42.74 | 7.16 | 50.10 |
| BL6 Control | 7.58 | 7.63 | 84.69 | 73.81 | 7.60 | 18.41 | 29.61 | 5.01 | 65.56 |
| Rx Chronic 6 wks | 10.90 | 83.69 | 5.39 | 4.62 | 10.35 | 85.03 | 6.70 | 10.13 | 83.17 |
| Rx Chronic 9 wks | 46.20 | 23.09 | 30.45 | 16.64 | 10.40 | 72.96 | 23.02 | 12.74 | 64.23 |

Table 26 shows a time profile of a single PA dose (1E-05 μl) on the nine T-cell marker series used in these studies. Again, the double positive cells (destined for apoptosis) as well as the activation series with CD8 are relatively refractory to treatment. PA treatment does modulate the activation CD4 series and mature cytotoxic T-cells (CD8+CD4−).

TABLE 26

Treatment with 0.00001 ug PA

| Percentage | CD69+CD4− | CD69+CD4+ | CD4+CD69− | CD4+CD8− | CD4+CD8+ | CD8+CD4− | CD69+CD8− | CD69+CD8+ | CD8+CD69− |
|---|---|---|---|---|---|---|---|---|---|
| 3 wks | 29.79 | 12.41 | 57.8 | 42.57 | 7.22 | 50.21 | 24.98 | 4.78 | 70.24 |
| 6 wks | 10.9 | 83.69 | 5.36 | 4.62 | 10.35 | 85.03 | 6.7 | 10.13 | 83.17 |
| 9 wks | 46.2 | 23.09 | 30.45 | 16.64 | 10.4 | 72.96 | 23.02 | 12.74 | 64.23 |
| 12 wks | 55.87 | 19.68 | 24.27 | 12.05 | 14.68 | 73.27 | 25.44 | 17.5 | 57.06 |
| Untreated BL 6 | 7.58 | 7.63 | 84.68 | 73.8 | 7.6 | 18.41 | 29.61 | 5.01 | 65.55 |
| Untreated BXSB | 44.34 | 19.69 | 35.78 | 15.92 | 13.91 | 70.16 | 22.54 | 13.69 | 63.76 |

In sum, the studies indicate that acute or chronic PA treatment regulated T-cell CD markers in BXSB mice in a dose and kinetic dependent manner, which correlate with the functional changes described above which include partial restoration of normal mitogenic responses (Example 5), reduction of autoantibody production (Example 6), and reduction of cytotoxicity response (Example 7). Thus, PA regulates the differentiation sequence of cells of lymphoid lineage.

What is claimed is:

1. A method for treating psoriasis in a subject with or at risk of psoriasis, comprising administering to the subject a monomeric protein A (PA) composition comprising an effective amount of protein A (PA), wherein the PA in the composition consists of monomeric protein A (PA) sufficient to treat the psoriasis.

2. A method for treating scleroderma in a subject with or at risk of scleroderma, comprising administering to the subject a monomeric protein A (PA) composition comprising an effective amount of protein A (PA), wherein the PA in the composition consists of monomeric protein A (PA) sufficient to treat the scleroderma.

3. A method for reducing an inflammatory response in a subject caused by psoriasis or scleroderma, comprising administering to the subject a monomeric protein A (PA) composition comprising an effective amount of protein A (PA), wherein the PA in the composition consists of monomeric protein A (PA) sufficient to reduce an inflammatory response caused by psoriasis or scleroderma.

4. The method of claim 3, wherein the inflammatory response is chronic or acute.

5. A method for treating inflammation in a subject caused by psoriasis or scleroderma, comprising administering to the subject a monomeric protein A (PA) composition comprising an effective amount of protein A (PA), wherein the PA in the composition consists of monomeric protein A (PA) sufficient to reduce the inflammation caused by psoriasis or scleroderma.

6. The method of claim 5, wherein the inflammation is chronic or acute.

7. The method of claim 1, wherein the method results in a reduction in severity of a symptom of psoriasis.

8. The method of claim 2, wherein the method results in a reduction in severity of a symptom of scleroderma.

9. The method of claim 3, wherein the method results in a reduction in severity of a symptom of the inflammatory response.

10. The method of claim 5, wherein the method results in a reduction in severity of inflammation.

11. The method of claim 7, wherein the symptom comprises swelling, pain, skeletal joint stiffness, or tissue or cell damage.

12. The method of claim 8, wherein the symptom comprises swelling, pain, headache, fever, nausea, skeletal joint stiffness, or tissue or cell damage.

13. The method of claim 9, wherein the symptom comprises swelling, pain, headache, fever, nausea, skeletal joint stiffness, or tissue or cell damage.

14. The method of claim 10, wherein the symptom comprises swelling, pain, headache, fever, nausea, skeletal joint stiffness, or tissue or cell damage.

15. The method of claim 1, wherein the subject is a human.

16. The method of claim 2, wherein the subject is a human.

17. The method of claim 3, wherein the subject is a human.

18. The method of claim 5, wherein the subject is a human.

19. The method of claim 1, 2, 3 or 5, wherein the monomeric PA composition is administered systemically.

20. The method of claim 1, 2, 3 or 5, wherein the monomeric PA composition is administered locally.

21. The method of claim 1, 2, 3 or 5, wherein the monomeric PA composition is administered intravenously, intramuscularly, intraperitoneally, intradermally, subcutaneously, intracavity, transdermally, parenterally, or transmucosally.

* * * * *